(12) United States Patent
Ferrandis et al.

(10) Patent No.: US 7,214,533 B2
(45) Date of Patent: May 8, 2007

(54) POLYNUCLEOTIDE USEFUL FOR MODULATING CANCER CELL PROLIFERATION

(75) Inventors: Eric Ferrandis, Saint Remy les Chevreuse (FR); José-Antonio Camara Y Ferrer, Paris (FR); Jean Martinez, Caux (FR); Christophe Thurieau, Paris (FR)

(73) Assignees: Societe de Conseils de Recherches Et d'Applications Scientifiques (S.C.R.A.S.), Paris (FR); Centre National de la Rescherche Scientifique (C.N.R.S.), Paris (FR)

( * ) Notice: Subject to any disclaimer, the term of this patent is extended or adjusted under 35 U.S.C. 154(b) by 499 days.

(21) Appl. No.: 10/467,436

(22) PCT Filed: Mar. 1, 2002

(86) PCT No.: PCT/FR02/00740

§ 371 (c)(1),
(2), (4) Date: Jan. 9, 2004

(87) PCT Pub. No.: WO02/070700

PCT Pub. Date: Sep. 12, 2002

(65) Prior Publication Data

US 2004/0197783 A1    Oct. 7, 2004

(30) Foreign Application Priority Data

Mar. 1, 2001   (FR)   .................................. 01 02801

(51) Int. Cl.
    *C12N 15/00*   (2006.01)
(52) U.S. Cl. .................. 435/320.1; 435/325; 536/23.5; 536/23.1; 530/350
(58) Field of Classification Search ............... 536/23.5, 536/23.1; 530/350; 435/320.1, 325; 424/277.1; 514/2

See application file for complete search history.

(56) References Cited

FOREIGN PATENT DOCUMENTS

WO    0069454    11/2000

OTHER PUBLICATIONS

Database EMBL 'Online! HSM802477, Feb. 18, 2002, Database accession No. AL157485, XP002186635.
Database EMBL 'Online! HSM802912, Jan. 12, 2001, Database accession No. AL512709 XP002186637.
Database EMBL 'Online! Feb. 22, 2002, Database accession No. AK000755, XP002186636.
Fan Saijun et al, "BRCA1 . . . Proteins", ONCOGENE, vol. 16, No. 23, Jun. 11, 1998, pp. 3069-3082.

*Primary Examiner*—Stephen Rawlings
(74) *Attorney, Agent, or Firm*—Charles A. Muserlian

(57) ABSTRACT

The invention concerns a novel protein modulating cancer cell proliferation. The proteins encoded by the polynucleotides of the invention enable to determine the degree of malignity of abnormal cell proliferation.

8 Claims, 3 Drawing Sheets

A                                    B

```
                            SEQUENCE LISTING

<160> NUMBER OF SEQ ID NOS: 9

<210> SEQ ID NO 1
<211> LENGTH: 576
<212> TYPE: DNA
<213> ORGANISM: Homo sapiens
<220> FEATURE:
<221> NAME/KEY: modified_base
<222> LOCATION: (9)
<223> OTHER INFORMATION: a, t, c, g, unknown or other
<220> FEATURE:
<221> NAME/KEY: modified_base
<222> LOCATION: (131)
<223> OTHER INFORMATION: a, t, c, g, unknown or other
<220> FEATURE:
<221> NAME/KEY: modified_base
<222> LOCATION: (541)
<223> OTHER INFORMATION: a, t, c, g, unknown or other
<220> FEATURE:
<221> NAME/KEY: modified_base
<222> LOCATION: (552)
<223> OTHER INFORMATION: a, t, c, g, unknown or other
<220> FEATURE:
<221> NAME/KEY: modified_base
<222> LOCATION: (571)
<223> OTHER INFORMATION: a, t, c, g, unknown or other

<400> SEQUENCE: 1
ctccatgana tgccactgtt cctgaccagc cgaagtccag gcaggggag gtttccttgt      60 ccaggaggga gaggacctcc accctctgac ctttcagttt tccatagcag cccagtgtga   120
agctcggcag ngggtgggca gggcatcagg acaagatgaa gatgctggct ctggaatgag   180
gactcccctt ggcataaggg gtagtggctg gcagaggttg cccagctctt ttggaggcca   240
cagggaatag aggtggggtg gtgcttccgt tcctgtgagg cccgcccccc tgagcccccct   300 ccgtctgctt cttgtttggc agaaatagat gtggggcaca gcctaagaat gatgggaatc   360
tgcccaagct gtgccctctg gggaaatgaa atcttgctcc tcgtgcagct tccccttttc   420
ccttgcgggg tgggggctgg gggtgccaag gctccaccct tggaaggggt tgctggggtg   480
ccaagctcca acctttgctc gctggcagaa ggaaggaagc acctcctgta tctttcaggg   540
ncctgaagcc antttgcctc agagaagaga nagtcc                               576

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: 5' primer

<400> SEQUENCE: 2
ctgacctttc agttttccat agc                                              23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: 3' primer

<400> SEQUENCE: 3
atctatttct gccaaacaag aa                                               22
```

<210> SEQ ID NO 4
<211> LENGTH: 1009
<212> TYPE: DNA
<213> ORGANISM: Homo sapiens
<220> FEATURE:
<223> OTHER INFORMATION: GenBank Acc. No. AK000755

<400> SEQUENCE: 4

| | | | | | |
|---|---|---|---|---|---|
| aggagggtct | gaaggtggga | gggcagctcc | atgagcagcc | actgttcctg | accagccgaa | 60 |
| gtgccaggca | gggggaggtt | tccatgtcca | ggagggagag | gacctccacc | ctctgacctt | 120 |
| tcagttttcc | atagcagccc | agtgtgaagc | tcggcggggg | tgggcagggc | atcaggacaa | 180 |
| gatgaagatg | ctggctctgg | aatgaggact | cccccttgggc | taagggtag | tggctggcag | 240 |
| aggttgccca | gctctttttgg | aggccacagg | gaatagaggt | gggtggtgc | ttccgttcct | 300 |
| gtgaggcccg | ccccctgag | cccctcgtc | tgcttcttgt | ttggcagaaa | tagatgtggg | 360 |
| gcacagcccc | tagatgatgg | gaatctgccc | aagctgtgtc | ctctggggaa | tgaaatcttg | 420 |
| ctcctcatgc | agcttcccct | ttcccttgcg | gggtggggc | tgggggtgcc | aaggctccac | 480 |
| ccttggaggg | ggttgctggg | ggtgccaagg | ctccaccctt | tgctcgctgg | gcagagggaa | 540 |
| ggaagcacct | ccctgtatgc | tctgcagggg | ccctgcagg | ccactttgcc | tcagaggaag | 600 |
| gaggagaggt | cccctgggaa | aatgcgcaca | cacacacaca | cacacacacg | cacacacaca | 660 |
| cgcacatgca | cacacgcacg | catgcacaca | cacacacata | tgtgcagggg | tgcagcctaa | 720 |
| gtcagtggag | ccaggactgg | ctgcgcagct | gggcctgccc | cattcttgga | gtccccaggg | 780 |
| aatgagcctc | aggatccact | tcgtcccttg | tttctaagcc | aggctgcacg | gccgttcctg | 840 |
| ggtgtgaaag | cattctgtcc | tgtctccagt | cagagggaac | cgcccccaaa | ctagaaagct | 900 |
| aatttcccccc | gaaggttcat | gaagccgagag | gcatgccctt | gggggttggt | cgggagaagg | 960 |
| gtgagaggca | gtgctgtgga | agggggcctgg | cccctgctgc | ctgcgattc | | 1009 |

<210> SEQ ID NO 5
<211> LENGTH: 1055
<212> TYPE: DNA
<213> ORGANISM: Homo sapiens

<400> SEQUENCE: 5

| | | | | | |
|---|---|---|---|---|---|
| aggagggtct | gaaggtggga | gggcagctcc | atgagcagcc | actgttcctg | accagccgaa | 60 |
| gtgccaggca | gggggaggtt | tccatgtcca | ggagggagag | gacctccacc | ctctgacctt | 120 |
| tcagttttcc | atagcagccc | agtgtgaagc | tcggcggggg | tgggcagggc | atcaggacaa | 180 |
| gatgaagatg | ctggctctgg | aatgaggact | cccccttgggc | taagggtag | tggctggcag | 240 |
| aggttgccca | gctctttttgg | aggccacagg | gaatagaggt | gggtggcaa | caggaaatag | 300 |
| ggtgtgggct | gtagaccata | gtgggtgggg | tggtgcttcc | gttcctgtga | ggcccgcccc | 360 |
| cctgagcccc | ctcgtctgct | tcttgtttgg | cagaaataga | tgtggggcac | agccctaga | 420 |
| tgatgggaat | ctgcccaagc | tgtgtcctct | ggggaatgaa | atcttgctcc | tcatgcagct | 480 |
| tcccctttcc | cttgcggggt | ggggctggg | ggtgccaagg | ctccaccctt | ggaggggggtt | 540 |
| gctgggggtg | ccaaggctcc | accctttgct | cgctgggcag | agggaaggaa | gcacctccct | 600 |
| gtatgctctg | caggggcccc | tgcaggccac | tttgcctcag | aggaaggagg | agaggtcccc | 660 |
| tgggaaaatg | cgcacacaca | cacacacaca | cacgcacaca | cacgca | catgcacaca | 720 |
| cgcacgcatg | cacacacaca | cacatatgtg | caggggtgca | gcctaagtca | gtggagccag | 780 |
| gactggctgc | gcagctgggc | ctgccccatt | cttggagtcc | ccaggaatg | agcctcagga | 840 |

```
tccacttcgt cccttgtttc taagccaggc tgcacggccg ttcctgggtg tgaaagcatt      900
ctgtcctgtc tccagtcaga gggaaccgcc cccaaactag aaagctaatt tcccccgaag      960
gttcatgaag ccagaggcat gcccttgggg gttggtcggg agaagggtga gaggcagtgc     1020
tgtggaaggg gcctggcccc tgctgcctgc gattc                                1055
```

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: 5' primer

<400> SEQUENCE: 6
gcaagcttgc ggggaggag gaggg                                              25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: 3' primer

<400> SEQUENCE: 7
cggaattccc gggggaatc gcag                                               24

<210> SEQ ID NO 8
<211> LENGTH: 147
<212> TYPE: PRT
<213> ORGANISM: Homo sapiens

<400> SEQUENCE: 8
```

```
Met Met Gly Ile Cys Pro Ser Cys Val Leu Trp Gly Met Lys Ser Cys
  1               5                  10                  15

Ser Ser Cys Ser Phe Pro Phe Pro Leu Arg Gly Gly Gly Trp Gly Cys
             20                  25                  30

Gln Gly Ser Thr Leu Gly Gly Gly Cys Trp Gly Cys Gln Gly Ser Thr
         35                  40                  45

Leu Cys Ser Leu Gly Arg Gly Lys Glu Ala Pro Cys Met Leu Cys
     50                  55                  60

Arg Gly Pro Cys Arg Pro Leu Cys Leu Arg Gly Arg Arg Gly Pro
 65                  70                  75                  80

Leu Gly Lys Cys Ala His Thr His Thr His Thr His Ala His Thr His
                 85                  90                  95

Ala His Ala His Thr His Ala Cys Thr His Thr His Ile Cys Ala Gly
                100                 105                 110

Val Gln Pro Lys Ser Val Glu Pro Gly Leu Ala Ala Gln Leu Gly Leu
            115                 120                 125

Pro His Ser Trp Ser Pro Gln Gly Met Ser Leu Arg Ile His Phe Val
        130                 135                 140

Pro Cys Phe
145
```

```
<210> SEQ ID NO 9
<211> LENGTH: 444
<212> TYPE: DNA
<213> ORGANISM: Homo sapiens

<400> SEQUENCE: 9
atgatgggaa tctgcccaag ctgtgtcctc tggggaatga atcttgctc ctcatgcagc       60
```

```
ttcccctttc ccttgcgggg tgggggctgg gggtgccaag gctccaccct tggaggggt      120 tgctgggggt gccaaggctc cacccttttgc tcgctgggca gagggaagga agcacctccc    180
tgtatgctct gcagggcccc ctgcaggcca ctttgcctca gaggaaggag gagaggtccc     240
ctgggaaaat gcgcacacac acacacacac acacacgcac acacacacgc acatgcacac    300
acgcacgcat gcacacacac acacatatgt gcaggggtgc agcctaagtc agtggagcca    360
ggactggctg cgcagctggg cctgccccat tcttggagtc cccagggaat gagcctcagg    420
atccacttcg tcccttgttt ctaa                                            444
```

POLYNUCLEOTIDE USEFUL FOR MODULATING CANCER CELL PROLIFERATION

This application is a 371 of PCT/FR02/00740 filed Mar. 1, 2002.

The present invention relates to a new protein modulating cancer cell proliferation. Thanks to the proteins coded by the polynucleotides of sequences SEQ.ID.NO. 4, SEQ.ID.NO. 5 and SEQ.ID.NO. 9 described below, it is also possible to determine the degree of malignancy of abnormal cell proliferation.

STATE OF THE ART

Cancer is a major health problem in the world. Although significant progress has been made in the last years in the detection and treatment of cancer, no vaccine or other universal treatment method for the prevention or treatment of cancer currently exists. Management of the disease involves the combination of as early as possible diagnosis and aggressive treatment including a variety of elements such as surgery, radiotherapy, chemotherapy or also hormone therapy. The evolution of the treatment for a given cancer is often selected on the basis of prognosis parameters comprising an analysis of specific markers of tumors. However, the use of established markers often leads to a result which is difficult to interpret and increased mortality continues to be observed in numerous cancer patients.

The breast and prostate cancers are the most frequent malignant tumors. In the United States, 400,000 new cases are diagnosed each year and approximately 100,000 men and women die every year of their disease (Harris et al., *New Eng. J. Med.* (1992), 327, 319, 390 and 473).

It is recognized that these diseases appear during a multi-factorial process involving mutations in a restricted number of genes, perhaps 10 or less. These mutations lead to a change of growth and modulation of cell proliferation of tissues allowing them to grow independently of normal cell controls, to form metastases and avoiding immune surveillance. The classes of genes involved in breast and prostate cancers can be highly specific to these classes of tumors. In particular, the mutations in the genes involved in hormonal responses (receptors and ligands of the class of oestrogens, progesterone or also testosterone) are particularly important as they probably drive the cells to proliferate by making them refractory to the anti-tumorous effect of these hormones.

Moreover, changes in the genes coding for growth factors, signal translation molecules as well for as transcription factors are frequently involved and have alterations which are themselves involved in tumor development and progression (King, *Nature Genetics* (1992), 2.125).

To this day an unresolved question is the nature of the changes of gene expression which appear in human tumorous cells in an irreversible manner leading to cell differentiation. This information is nevertheless very important for the definition, on the molecular level, of the regulation diagrams of gene expression involved in cell growth and differentiation of the human cells of prostate and breast cancers. There therefore exists an urgent need to identify the gene sequences involved in the irreversible terminal differentiation rendezvous.

Very recently, when the Applicant was already in possession of the invention described hereafter, the sequence SEQ.ID.NO. 4 was disclosed in the Genbank database under the access number AK000755 and identification number 7021039, without, however, an indication of the activity of the proteins which can be coded by this sequence.

THE INVENTION

A subject of the present invention is an isolated polynucleotide comprising the polynucleotide sequence SEQ.ID.NO. 5. A subject is also an anti-sense polynucleotide comprising the complementary sequence to that of said isolated polynucleotide comprising the polynucleotide sequence SEQ.ID.NO. 5.

The invention also relates to an isolated polynucleotide comprising at least one fragment of the polynucleotide sequence SEQ.ID.NO. 5, said polynucleotide being such that it codes for a polypeptide having at least one immunological and/or biological activity characteristic of a protein associated with the modulation of cell proliferation. In particular, the invention relates to the isolated polynucleotide of nucleotide sequence SEQ.ID.NO. 9 or the isolated polynucleotide of nucleotide sequence complementary to the nucleotide sequence SEQ.ID.NO. 9.

Moreover a subject of the invention is an isolated polypeptide comprising at least one fragment of the protein coded by the polynucleotide sequence SEQ.ID.NO. 5 or by a complementary sequence of the polynucleotide sequence SEQ.ID.NO. 5, said isolated polypeptide having at least one immunological and/or biological activity characteristic of a protein associated with the modulation of cell proliferation. Preferably, said isolated polypeptide has a fragment having a immunological activity characteristic of a protein associated with the modulation of cell proliferation.

In particular, the invention relates to the protein of sequence SEQ.ID.NO. 8 (described below) coded by the fragment of the polynucleotide of polynucleotide sequence SEQ.ID.NO. 5 contained between the bases in positions 420 (initiation codon ATG coding for a methionine) and 861 (stop codon UAA), i.e. by the polynucleotide sequence SEQ.ID.NO. 9 (described below).

The invention also relates to an expression vector comprising an isolated polynucleotide comprising at least one fragment of the polynucleotide sequence SEQ.ID.NO. 5 or of the complementary sequence of the polynucleotide sequence SEQ.ID.NO. 5, the polypeptide coded by said isolated polynucleotide having at least one immunological and/or biological activity characteristic of a protein associated with the modulation of cell proliferation. Similarly it relates to a host cell transformed or transfected with said expression vector.

A subject of the invention is also a monoclonal antibody, or a fragment of an antigen bond of the latter, which specifically binds an isolated polypeptide such as described previously, and in particular a monoclonal antibody, or a fragment of an antigen bond of the latter, which specifically binds the protein of sequence SEQ.ID.NO. 8.

Moreover, the invention relates, as a medicament, to an isolated polypeptide comprising at least one fragment of the protein coded by the polynucleotide sequence SEQ.ID.NO. 5 or by a complementary sequence of the polynucleotide sequence SEQ.ID.NO. 5, said isolated polypeptide having at least one immunological and/or biological activity characteristic of a protein associated with the modulation of cell proliferation. In particular, said fragment can be the fragment coded by the polynucleotide of nucleotide sequence SEQ.ID.NO. 9 or by the complementary sequence of the polynucleotide sequence SEQ.ID.NO. 9, in other words the protein of sequence SEQ.ID.NO. 8. Similarly, it relates, as a medicament, to an isolated polypeptide comprising at least one fragment of the protein coded by the polynucleotide sequence SEQ.ID.NO. 4 or by a complementary sequence of the polynucleotide sequence SEQ.ID.NO. 4, said isolated polypeptide having at least one immunological and/or biological activity characteristic of a protein associated with the modulation of cell proliferation.

The invention also relates, as a medicament, to a monoclonal antibody, or a fragment of an antigen bond of the latter, which specifically binds an isolated polypeptide comprising at least one fragment of the protein coded by the polynucleotide sequence SEQ.ID.NO. 4 or SEQ.ID.NO. 5 or by a complementary sequence of the polynucleotide sequence SEQ.ID.NO. 4 or SEQ.ID.NO. 5, said isolated polypeptide having at least one immunological and/or biological activity characteristic of a protein associated with the modulation of cell proliferation.

In particular, the invention relates, as a medicament, to a monoclonal antibody, or a fragment of an antigen bond of the latter, which specifically binds an isolated polypeptide coded by the polynucleotide of nucleotide sequence SEQ.ID.NO. 9 or by the complementary sequence of the polynucleotide sequence SEQ.ID.NO. 9 (in other words the protein of sequence SEQ.ID.NO. 8).

The invention relates moreover to a pharmaceutical composition comprising an isolated polypeptide comprising:
either a fragment of the protein coded by the polynucleotide sequence SEQ.ID.NO. 5 or by a complementary sequence of the polynucleotide sequence SEQ.ID.NO. 5,
or a fragment of the protein coded by the polynucleotide sequence SEQ.ID.NO. 4 or by a complementary sequence of the polynucleotide sequence SEQ.ID.NO. 4, said isolated polypeptide having at least one immunological and/or biological activity characteristic of a protein associated with the modulation of cell proliferation;

said composition comprising moreover one or more pharmaceutically acceptable excipients.

In particular, a subject of the invention is a pharmaceutical composition comprising the protein coded by the polynucleotide sequence SEQ.ID.NO. 9 or by the complementary sequence of the polynucleotide sequence SEQ.ID.NO. 9 (in other words the protein of sequence SEQ.ID.NO. 8) with one or more pharmaceutically acceptable excipients.

Alternatively, a pharmaceutical composition according to the invention comprises a monoclonal antibody, or a fragment of an antigen bond of the latter, which specifically binds an isolated polypeptide comprising at least one fragment of the protein coded by the polynucleotide sequence SEQ.ID.NO. 4 or SEQ.ID.NO. 5 or by a complementary sequence of the polynucleotide sequence SEQ.ID.NO. 4 or SEQ.ID.NO. 5, said isolated polypeptide having at least one immunological and/or biological activity characteristic of a protein associated with the modulation of cell proliferation, said composition comprising moreover one or more pharmaceutically acceptable excipients.

In particular, the invention relates to a pharmaceutical composition comprising a monoclonal antibody, or a fragment of an antigen bond of the latter, which specifically binds the protein coded by the polynucleotide sequence SEQ.ID.NO. 9 or by the complementary sequence of the polynucleotide sequence SEQ.ID.NO. 9 (in other words the protein of sequence SEQ.ID.NO. 8) with pharmaceutically acceptable excipients.

According to a preferred variant, said pharmaceutical compositions also comprises an immune response activator (which can be an adjuvant).

An additional subject of the invention is the use, for preparing a medicament intended to treat a proliferative disease, of an isolated polypeptide comprising:
either a fragment of the protein coded by the polynucleotide sequence SEQ.ID.NO. 5 or by a complementary sequence of the polynucleotide sequence SEQ.ID.NO. 5,
or a fragment of the protein coded by the polynucleotide sequence SEQ.ID.NO. 4 or by a complementary sequence of the polynucleotide sequence SEQ.ID.NO. 4, said isolated polypeptide having at least one immunological and/or biological activity characteristic of a protein associated with the modulation of cell proliferation.

In particular, the invention relates to the use, for preparing a medicament intended to treat a proliferative disease, of an isolated polypeptide coded by the polynucleotide sequence SEQ.ID.NO. 9 or by the complementary sequence of the polynucleotide sequence SEQ.ID.NO. 9 (in other words, the protein of sequence SEQ.ID.NO. 8) with one or more pharmaceutically acceptable excipients.

Another subject of the invention is the use of an isolated polynucleotide comprising:
the polynucleotide sequence SEQ.ID.NO. 5, or
the polynucleotide sequence SEQ.ID.NO. 4, or also
the polynucleotide sequence SEQ.ID.NO. 9, for preparing a medicament intended to treat a proliferative disease.

Preferably, the isolated polynucleotide used will consist of a polynucleotide of polynucleotide sequence SEQ.ID.NO. 4, SEQ.ID.NO. 5 or SEQ.ID.NO. 9.

Said isolated polynucleotide used is preferably present in a viral vector, said viral vector being for example selected from the group consisting of an adenovirus, a combined adenovirus, a retrovirus and a pox virus.

Alternatively, still according to the present invention, a monoclonal antibody, or a fragment of an antigen bond of the latter, which specifically binds an isolated polypeptide comprising at least one fragment of the protein coded by the polynucleotide sequence SEQ.ID.NO. 4 or SEQ.ID.NO. 5 or by a complementary sequence of the polynucleotide sequence SEQ.ID.NO. 4 or SEQ.ID.NO. 5, said isolated polypeptide having at least one immunological and/or biological activity characteristic of a protein associated with the modulation of cell proliferation, can be used for preparing a medicament intended to treat a proliferative disease.

In particular, a monoclonal antibody, or a fragment of an antigen bond of the latter, which specifically binds an isolated polypeptide coded by the polynucleotide sequence SEQ.ID.NO. 9 or by the complementary sequence to the polynucleotide sequence SEQ.ID.NO. 9 (in other words, a monoclonal antibody, or a fragment of an antigen bond of the latter, which specifically binds the protein of sequence SEQ.ID.NO. 8), can be used for preparing a medicament intended to treat a proliferative disease.

According to preferred variants of the uses mentioned above, the proliferative disease to be treated by the polypeptide or the polynucleotide described previously is a cancer. According to yet more preferred variants, the cancer is chosen from the group consisting of prostate cancer, breast cancer, lung cancer and colorectal cancer.

Moreover, the invention offers a method for determining whether a tumor in a patient is malignant, said method comprising the determination, in a tumor sample obtained from a patient, of the concentration of an isolated polypeptide comprising at least:

either a fragment of the protein coded by the polynucleotide sequence SEQ.ID.NO. 5 or by a complementary sequence of the polynucleotide sequence SEQ.ID.NO. 5, or a fragment of the protein coded by the polynucleotide sequence SEQ.ID.NO. 4 or by a complementary sequence of the polynucleotide sequence SEQ.ID.NO. 4, said isolated polypeptide having at least one immunological and/or biological activity characteristic of a protein associated with the modulation of cell proliferation.

In particular, said determination method can have as its subject the determination, in a tumor sample obtained from a patient, of the concentration of isolated polypeptide coded by the polynucleotide sequence SEQ.ID.NO. 9 or by the complementary sequence to the polynucleotide sequence SEQ.ID.NO. 9 (in other words, the concentration of protein of sequence SEQ.ID.NO. 8).

According to a preferred variant of the method mentioned above, said method comprises the bringing into contact of the tumor sample with a monoclonal antibody which specifically recognises the isolated polypeptide mentioned previously (and in particular isolated polypeptide coded by the polynucleotide sequence SEQ.ID.NO. 9 or by the complementary sequence to the polynucleotide sequence SEQ.ID.NO. 9 (in other words, of the concentration of protein of sequence SEQ.ID.NO. 8)).

The invention also relates to a method for determining whether a tumor in a patient is malignant, said method comprising the determination, in a biological sample obtained from a patient, of the concentration:

of polynucleotide of polynucleotide sequence SEQ.ID.NO. 5 or SEQ.ID.NO. 4, or of polynucleotide the nucleotide sequence of which is a fragment of the polynucleotide sequence SEQ.ID.NO. 5 or SEQ.ID.NO. 4, said fragment coding for an isolated polypeptide having at least one immunological and/or biological activity characteristic of a protein associated with the modulation of cell proliferation.

In particular, said method comprises the determination, in a biological sample obtained from a patient, of the concentration of isolated polypeptide coded by the polynucleotide sequence SEQ.ID.NO. 9 or by the complementary sequence to the polynucleotide sequence SEQ.ID.NO. 9 (in other words, of the concentration of protein of sequence SEQ.ID.NO. 8).

According to a preferred variant of this last method, said method comprises:

(a) the preparation of molecules of cDNA from molecules of RNA of the tumor sample, then
(b) the specific amplification of molecules of cDNA which are capable of coding for at least one portion of the polypeptide.

The invention also offers a method for monitoring the progression or regression of the disease in a patient suffering from a cancer, said method comprising:

(a) the determination, repeated at intervals chosen over time, in a biological sample obtained from a patient, of the concentration of isolated polypeptide comprising at least:
  either a fragment of the protein coded by the polynucleotide sequence SEQ.ID.NO. 5 or by a complementary sequence of the polynucleotide sequence SEQ.ID.NO. 5,
  or a fragment of the protein coded by the polynucleotide sequence SEQ.ID.NO. 4 or by a complementary sequence of the polynucleotide sequence SEQ.ID.NO. 4,
  said isolated polypeptide having at least one immunological and/or biological activity characteristic of a protein associated with the modulation of cell proliferation, and
(b) the comparison, over time, of the concentrations determined in (a).

In particular, said method for monitoring the progression or regression of the disease in a patient suffering from cancer will comprise, in its Stage (a), the determination repeated at intervals chosen over time, in a biological sample obtained from a patient, of the concentration of isolated polypeptide coded by the polynucleotide sequence SEQ.ID.NO. 9 or by the complementary sequence to the polynucleotide sequence SEQ.ID.NO. 9 (in other words, of the concentration of protein of sequence SEQ.ID.NO. 8).

Stage (a) of the above method will preferably comprise the bringing into contact of a portion of the biological sample with a monoclonal antibody which specifically recognises said polypeptide (in particular the protein of sequence SEQ.ID.NO. 8). According to a preferred variant of the above method, the biological sample obtained from the patient is moreover a portion of tumor.

Still according to the invention, another method for monitoring the progression or regression of the disease in a patient suffering from cancer will comprise the following stages:

(a) the determination, repeated at intervals chosen over time, in a biological sample obtained from a patient, of the concentration of RNA coding for an isolated polypeptide comprising at least:
  either a fragment of the protein coded by the polynucleotide sequence SEQ.ID.NO. 5 or by a complementary sequence of the polynucleotide sequence SEQ.ID.NO. 5,
  or a fragment of the protein coded by the polynucleotide sequence SEQ.ID.NO. 4 or by a complementary sequence of the polynucleotide sequence SEQ.ID.NO. 4,
  said isolated polypeptide having at least one immunological and/or biological activity characteristic of a protein associated with the modulation of cell proliferation, and
(b) the comparison, over time, of the concentrations determined in (a).

In particular, said method for monitoring the progression or regression of the disease in a patient suffering from cancer will include, in its Stage (a), the determination repeated at intervals chosen over time, in a biological sample obtained from a patient, of the concentration of RNA coding for an isolated polypeptide coded by the polynucleotide sequence SEQ.ID.NO. 9 or by the complementary sequence to the polynucleotide sequence SEQ.ID.NO. 9 (in other words, of the concentration of RNA coding for the protein of sequence SEQ.ID.NO. 8).

According to a preferred variant of the monitoring method described above, Stage (a) will preferably comprise:

(i) the preparation of molecules of cDNA from molecules of RNA in the biological sample, and
(ii) the specific amplification of molecules of cDNA which are capable of coding at least for a portion of said isolated polypeptide.

All the determination and/or monitoring methods described above are tools which allow the doctor, after analysis of the results, to formulate their diagnosis as to the gravity and/or the progression or regression of the tumors of the concerned patient.

Moreover a subject of the invention is a kit for the diagnosis of proliferative diseases comprising:
(1) a monoclonal antibody which specifically binds an isolated polypeptide comprising at least one fragment of the protein coded by the polynucleotide sequence SEQ.ID.NO. 5 or SEQ.ID.NO. 4, or by a complementary sequence of the polynucleotide sequence SEQ.ID.NO. 5 or SEQ.ID.NO. 4,
(2) a second monoclonal antibody or a fragment of the latter which binds either to a monoclonal antibody as defined in (1), or with the isolated polypeptide as defined in (1), said second monoclonal antibody being conjugated to a tag moiety.

In particular, said kit for the diagnosis of proliferative diseases can be chosen such that the fragment of the protein coded by the polynucleotide sequence SEQ.ID.NO. 5 is the isolated polypeptide coded by the polynucleotide sequence SEQ.ID.NO. 9 or by the complementary sequence of the polynucleotide sequence SEQ.ID.NO. 9 (in other words, the protein of sequence SEQ.ID.NO. 8).

Preferably, the tag moiety of the above diagnosis kit is selected from the group comprising radioisotopes, fluorescent groups, luminescent groups, enzymes, biotin and staining particles.

Moreover, the invention offers a method for the preparation of an isolated polypeptide comprising at least one fragment of the protein coded by the polynucleotide sequence SEQ.ID.NO. 5 or by a complementary sequence of the polynucleotide sequence SEQ.ID.NO. 5, said isolated polypeptide having at least one immunological and/or biological activity characteristic of a protein associated with the modulation of cell proliferation, said preparation method comprising the following successive stages:
(a) culture, under conditions suitable for obtaining the expression of said polypeptide of a host cell transformed or transfected with an expression vector comprising an isolated polynucleotide comprising at least one fragment of the protein coded by the polynucleotide sequence SEQ.ID.NO. 5 or by a complementary sequence of the polynucleotide sequence SEQ.ID.NO. 5, said isolated polypeptide having at least one immunological and/or biological activity characteristic of a protein associated with the modulation of cell proliferation, and
(b) isolation of the polypeptide from the cultures of host cells.

In particular, a subject of said method is the preparation of the isolated polypeptide coded by the polynucleotide sequence SEQ.ID.NO. 9 or by the complementary sequence of the polynucleotide sequence SEQ.ID.NO. 9 (in other words, the preparation of the protein of sequence SEQ.ID.NO. 8).

The present invention also offers a method for the identification of compounds capable of modulating cell growth and/or differentiation, which comprises the following successive stages:
(a) bringing into contact each candidate compound, under conditions and for a time sufficient to allow the candidate agent to bind with the polypeptide, with an isolated polypeptide comprising at least:
  either a fragment of the protein coded by the polynucleotide sequence SEQ.ID.NO. 5 or by a complementary sequence of the polynucleotide sequence SEQ.ID.NO. 5,
  or a fragment of the protein coded by the polynucleotide sequence SEQ.ID.NO. 4 or by a complementary sequence of the polynucleotide sequence SEQ.ID.NO. 4, said isolated polypeptide having at least one immunological and/or biological activity characteristic of a protein associated with the modulation of cell growth and/or differentiation, and
(b) detection of the binding of each candidate compound to said polypeptide and identification, from the candidate compounds, of the compounds capable of modulating cell growth and/or differentiation.

In particular, said method for the identification of compounds capable of modulating cell growth and/or differentiation will comprise, in its Stage (a), the bringing into contact of each candidate compound, under conditions and for a time sufficient to allow the candidate agent to bind to the polypeptide, with the isolated polypeptide coded by the polynucleotide sequence SEQ.ID.NO. 9 or by the complementary sequence of the polynucleotide sequence SEQ.ID.NO. 9 (in other words, with the protein of sequence SEQ.ID.NO. 8).

An alternative method for the identification of compounds capable of modulating cell growth and/or differentiation comprises the following successive stages:
(a) bringing into contact each candidate compound, under conditions and for a time sufficient to allow the candidate agent and the cell to interact, with a cell capable of expressing an isolated polypeptide comprising at least:
  either a fragment of the protein coded by the polynucleotide sequence SEQ.ID.NO. 5 or by a complementary sequence of the polynucleotide sequence SEQ.ID.NO. 5,
  or a fragment of the protein coded by the polynucleotide sequence SEQ.ID.NO. 4 or by a complementary sequence of the polynucleotide sequence SEQ.ID.NO. 4, said isolated polypeptide having at least one immunological and/or biological activity characteristic of a protein associated with the modulation of cell growth and/or differentiation, and
(b) determination of the effect of each candidate compound on the cell concentration of polypeptide and identification, from the candidate compounds, of the compounds capable of modulating cell growth and/or differentiation.

In particular, said alternative method will comprise, in its Stage (a), the bringing into contact of each candidate compound, under conditions and for a time sufficient to allow the candidate agent and the cell to interact, with a cell capable of expressing the isolated polypeptide coded by the polynucleotide sequence SEQ.ID.NO. 9 or by the complementary sequence of the polynucleotide sequence SEQ.ID.NO. 9 (in other words, a cell capable of expressing the protein of sequence SEQ.ID.NO. 8).

According to preferred embodiments of the identification methods of compounds capable of modulating the growth and/or differentiation described above, the candidate compounds will come from libraries of small molecules originating from combinatorial chemistry programs.

Moreover, the invention relates to a polynucleotide comprising an endogenous promoter or a regulation element of the protein associated with differentiation, in which the protein comprises a sequence coded by a polynucleotide sequence SEQ.ID.NO. 5 or by a complementary sequence of the polynucleotide sequence SEQ.ID.NO. 5.

The invention also relates to a polynucleotide comprising a tag gene under the control of the endogenous promoter or the regulation elements of the protein associated with the modulation of cell proliferation, in which the protein comprises a sequence coded by the polynucleotide sequence SEQ.ID.NO. 5 or by a complementary sequence of the polynucleotide sequence SEQ.ID.NO. 5. Similarly, the invention relates to a cell transformed or transfected with this last polynucleotide.

Moreover, the invention relates to a method for identifying the compounds capable of modulating the expression of the protein associated with the modulation of cell proliferation, which comprises the following successive stages:

(a) bringing into contact each candidate compound, under conditions and for a time sufficient to allow each candidate compound to interact with the promoter or the regulation element of the latter, with a cell transformed or transfected with a polynucleotide comprising a tag gene under the control of the endogenous promoter or the regulation elements of the protein associated with the modulation of cell proliferation, in which the protein comprises a sequence coded by the polynucleotide sequence SEQ.ID.NO. 5 or by a complementary sequence of the polynucleotide sequence SEQ.ID.NO. 5, (b) determination of the effects of each candidate compound on the concentration of tag protein produced by the cell, and identification of the compounds capable of modulating the expression of the protein associated with the modulation of cell proliferation.

According to a preferred embodiment of the method for the identification of compounds capable of modulating the expression of the protein associated with the modulation of cell proliferation described above, the candidate compounds come from libraries of small molecules originating from combinatorial chemistry programs.

The pharmacological properties obtained for the polynucleotides and polypeptides according to the invention render the latter suitable for pharmaceutical use. In fact, the isolated polypeptides comprising at least:

either a fragment of the protein coded by the polynucleotide sequence SEQ.ID.NO. 5 or by a complementary sequence of the polynucleotide sequence SEQ.ID.NO. 5, or a fragment of the protein coded by the polynucleotide sequence SEQ.ID.NO. 4 or by a complementary sequence of the polynucleotide sequence SEQ.ID.NO. 4, which have at least one immunological and/or biological activity characteristic of a protein associated with the modulation of cell proliferation, as well as the polynucleotides coding for said polypeptides, can, according to the invention, be administered to cancer patients in order to slow down the progression of their tumors or cause said tumors to regress.

In the above methods, the protein associated with the modulation of cell proliferation or differentiation can in particular be the isolated polypeptide coded by the polynucleotide sequence SEQ.ID.NO. 9 or by the complementary sequence of the polynucleotide sequence SEQ.ID.NO. 9 (in other words, the protein of sequence SEQ.ID.NO. 8).

The different elements mentioned above will become obvious to a person skilled in the art once the more detailed description of the different aspects of the invention are read.

BRIEF DESCRIPTION OF THE DRAWINGS

Finally.

DETAILED DESCRIPTION OF THE DIFFERENT ASPECTS OF THE INVENTION

Figure 1:
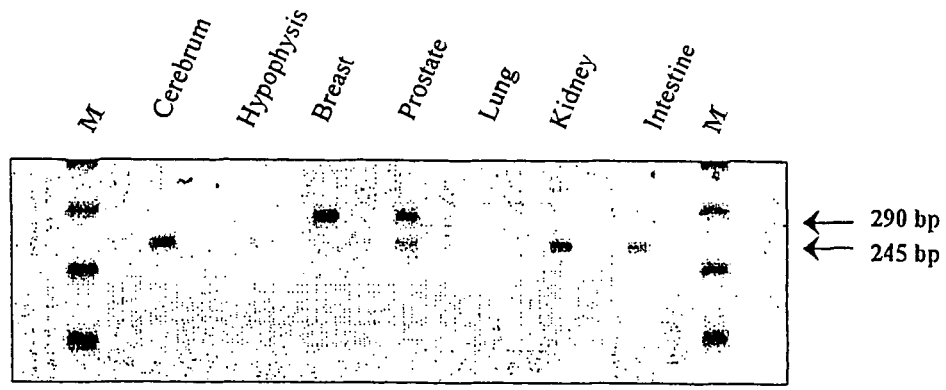
FIG. 1 represents the results obtained by PCR after separation on 1% agarose gel and visualization using ethidium bromide staining.

As mentioned above, the present invention is generally directed towards the products and the methods intended to modulate cell growth and to treat cancer. The present invention is based, in part, on the identification of "sequences associated with the modulation of cell proliferation" which are polypeptide and polynucleotide sequences associated with the modulation of cell proliferation. An mRNA associated with the differentiation is an mRNA which is present at a higher level in differentiated cells than in the corresponding non-differentiated cells (i.e. the level of mRNA is at least twice as high). A molecule of cDNA associated with the differentiation is a sequence corresponding to an mRNA associated with the differentiation (and/or a complementary sequence).

Such cDNA molecules can be prepared from preparations of RNA or mRNA using standard techniques, such as reverse transcription. Similarly, a protein or a polypeptide associated with the differentiation comprises the sequence coded by an mRNA associated with cell differentiation.

The pharmaceutical compositions described here can include one or more polypeptides, sequences of nucleic acids and/or antibodies. The polypeptides of the present invention include at least one portion of the protein associated with the modulation of cell proliferation or a variant of the latter. The nucleic acids sequences of the present invention include a DNA or RNA sequence which codes at least for a portion of such a polypeptide or which is complementary to a such a coding sequence.

The antibodies are proteins of the immune system or antigen binding fragments of the latter, which are capable of binding a portion of the polypeptides described above.

Alternatively, a composition can include one or more agents which modulate the expression of the gene associated with the modulation of cell proliferation.

Polynucleotides, Polypeptides and Proteins According to the Invention

In particular a subject of the present invention is the polynucleotides of sequence SEQ.ID.NO. 4, SEQ.ID.NO. 5 or SEQ.ID.NO. 9 as well as the polypeptide or the protein of sequence SEQ.ID.NO. 8.

The invention also comprises the polynucleotides having the polynucleotide sequences which are at least 75%, preferably at least 85% and also more preferentially at least 90% even 95%, homologous to the sequences of the polynucleotides described above, in particular to the sequences SEQ.ID.NO. 4, SEQ.ID.NO. 5 and SEQ.ID.NO. 9. This also applies mutatis mutandis to the other polynucleotides, polypeptides and proteins forming part of the invention, in particular to the protein of sequence SEQ.ID.NO. 8.

A subject of the present invention is isolated polynucleotides or polypeptides. A polynucleotide or a polypeptide is called "isolated" if it is taken out of its original environment. In particular, a polynucleotide or a polypeptide is isolated if it is separated from the biological material with which it coexisted in the natural system.

According to the invention, the polynucleotide sequences which code for the polypeptides or proteins of the invention, and the fragments or the fusion proteins of these polypeptides or proteins, can be used to generate molecules of recombinant DNA which direct the expression of these polypeptides or proteins, or an active portion of the latter, in appropriate host cells. Alternatively, polynucleotide sequences which hybridize with portions of the polynucleotide sequences according to the invention can also be used in nucleic acids hybridization tests, Southern blot, Northern blot, etc.

Because of the degeneration of the genetic code, other DNA sequences coding substantially for the amino acid sequence of the polypeptides or proteins of the invention can be used for the cloning and expression of said polypeptides or proteins. Such DNA sequences include those capable of hybridizing the polynucleotide sequences of the polynucleotides of the invention under certain stringency conditions which can be adjusted in several ways. For example, during polymerase chain reaction (PCR), the temperature at which the primers hybridize to the matrix or the concentrations of $MgCl_2$ in the reaction buffer, can be adjusted. During the use of fragments of radio-labelled DNA, or of oligonucleotides to probe membranes, the stringency can be adjusted by changing the ionic strengths of the washing solutions or by carefully controlling the washing temperature.

The invention comprises in particular the polynucleotides presenting an homology of at least 75% with the polynucleotide of sequence SEQ.ID.NO. 4, SEQ.ID.NO. 5 or SEQ.ID.NO. 9. The degree of homology expressed in % is calculated as follows:

$$100-100\times(N'/N)$$

with N' representing the number of nucleotides modified with respect to the sequence SEQ.ID.NO. 4, SEQ.ID.NO. 5 or SEQ.ID.NO. 9 and N the number of nucleotides of SEQ.ID.NO. 4, SEQ.ID.NO. 5 or SEQ.ID.NO. 9.

Preferentially, such an homologous nucleotide sequence hybridizes specifically with the complementary sequence to the sequence SEQ.ID.NO. 4, SEQ.ID.NO. 5 or SEQ.ID.NO. 9 under stringent conditions. The parameters defining the stringency conditions depend on the temperature at which 50% of the paired strands separate ($T_m$).

For the sequences comprising more than 30 bases, and according to Sambrook et al. (*Molecular cloning: A Laboratory Manual*, Cold Spring Harbor Laboratories, Cold Spring Harbor, N.Y., 1989), $T_m$ is defined by the relationship:

$$T_m=81.5+0.41\times(\%\ G+C)+16.6\times\log[\text{cations}]-0.63\times(\%\ \text{formamide})-(600/\text{number of bases})$$

For the present invention, the stringency conditions are called "strong" when a hybridization temperature of 10° C. below $T_m$ and hybridization buffers containing a solution 6×SSC (0.9 M sodium chloride and 0.09 M sodium citrate) are used. Under such conditions, the non-specific polynucleotide sequences do not hybridize with the polynucleotide of the complementary sequence to the sequence SEQ.ID.NO. 4, SEQ.ID.NO. 5 or SEQ.ID.NO. 9.

Altered DNA sequences which can be used according to the present invention include deletions, additions or substitutions of different nucleotide residues resulting in a sequence which codes the same product of the gene or equivalent function. The product of the gene can also contain deletions, additions or substitutions of the amino acid residues in the sequences of the proteins of the invention, which result in changes called silent, therefore producing polypeptides and proteins of equivalent function.

Such amino acid substitutions can be carried out on the basis of polarity, charge, solubility, hydrophobicity, hydrophilicity, and/or the amphipatic nature of the residues involved.

For example, negatively-charged amino acids include aspartic acid and glutamic acid, positively-charged amino acids include lysine and arginine, amino acids with polar groups having close hydrophobicity values include leucine, isoleucine, valine; glycine, alanine; asparagine, glutamine; serine, threonine; phenylalanine, tyrosine.

The DNA sequences of the present invention can be modified to alter the polynucleotide sequences according to the invention for numerous reasons including in a non-limitative manner alterations which modify the process and expression of the gene product. For example, mutations can be introduced using techniques well known to a person skilled in the art, for example directed mutagenesis, the insertion of new restriction sites, the alteration of glycosylations, phosphorylation, etc.

In particular, in certain expression systems such as yeast, the host cell can over-glycosylate the gene product. In such a system, it is preferable to alter the polynucleotide sequences to eliminate the glycosylation sites. Within the scope of the disclosure of the present invention, modified polynucleotide sequences linked to the heterologous sequences for coding a fusion protein also figure. The fusion protein can be modified to contain a cleavage site located between the sequence of the protein according to the invention (for example the sequence SEQ.ID.NO. 8) and the sequence of the heterologous protein, such that the sequence of the protein according to the invention can be cleaved from the heterologous part.

Polynucleotides Associated with the Modulation of Cell Proliferation

Any polynucleotide which codes for a polypeptide associated with the modulation of cell proliferation or a portion or a variant of the latter as described here is covered by the present invention. Such polynucleotides can be single-stranded (coding or anti-sense) or double-stranded and can be DNA (genomic, cDNA or synthetic) or RNA molecules.

The polynucleotides associated with differentiation can be prepared using any of the techniques available to a person skilled in the art. For example, such a polynucleotide can be amplified via a polymerase chain reaction (PCR) from cDNA prepared from cells or human tissues. For this approach, specific primers can be designed and ordered or synthesized; these primers are based on the sequence of said polynucleotide. An amplified portion can then be used to isolate the complete gene from a human genomic DNA bank or from a cDNA bank of whatever cell or whatever tissue, whether it is normal, tumorous or differentiated, thanks to techniques well known to a person skilled in the art and briefly mentioned below. Alternatively, a complete gene can be constructed from several PCR fragments. The cDNA molecules coding for a protein associated with differentiation, or a portion of the latter, can also be prepared by screening a cDNA bank obtained for example from the mRNA of cells or tissues. Such libraries are commercially available or can be prepared by using standard techniques (cf. Sambrook et al., *Molecular cloning: A Laboratory Manual*, Cold Spring Harbor Laboratories, Cold Spring Harbor, N.Y., 1989).

Alternatively, other screening techniques well known to a person skilled in the art can be used.

A molecule of cDNA associated with differentiation can be sequenced by using the standard enzyme techniques such as the Klenow fragment of DNA polymerase I, Sequenase X (US Biochemical Corp., Cleveland, Ohio, USA), Taq polymerase (Perkin Elmer, Foster City, Calif., USA), thermostable polymerase T7 (Amersham, Chicago, IT, USA) or a combination of recombinant polymerases and exonucleases with a rereading activity such as the Elongase amplification system (Gibco BRL, Gaithersburg, Md., USA). An automatic sequencing system can be used, using the instruments available from commercial suppliers such as Perkin Elmer and Pharmacia.

The partial sequence of a cDNA can be used to identify a polynucleotide sequence which codes for the complete protein associated with the modulation of cell proliferation by using standard techniques well known to a person skilled in the art.

Among these techniques, a cDNA library is screened by using one or more polynucleotide probes using the recombination properties of RecA (ClonCapture cDNA Selection Kit, Clontech Laboratories, USA).

For the hybridization techniques, a partial sequence can be radio-labelled (for example by nick translation or by labelling of the ends using $^{32}P$ or $^{33}P$) using standard techniques. A library of bacteria or bacteriophages is then screened by hybridization on filters containing denaturated bacterial colonies (or prints containing the phage plates) with the labelled probe (cf. Sambrook et al., *Molecular cloning: A Laboratory Manual*, Cold Spring Harbor Laboratories, Cold Spring Harbor, N.Y., 1989). The positive colonies or plates are then selected and amplified and the DNA is isolated for future analyses.

The complete sequence can then be determined by using standard techniques. The overlapping sequences are then assembled in a single continuous sequence. A molecule of complete cDNA can be generated by ligature of the fragments of interest by using standard techniques.

Alternatively, numerous techniques exist based on amplification for obtaining a complete coding sequence from a partial sequence of cDNA. Amongst these, amplification is generally carried out via PCR. All the kits which are commercially available can be used for the amplification stages. The primers can be designed by using, for example, software well known in the art. The nucleotide primers are preferably molecules of 20 to 30 nucleotides having a guanine and cytosine content of at least 50% and which hybridize with the target sequence at temperatures comprised between 50 and 72° C. The amplified region can be sequenced as described above and the overlapping sequences assembled in a continuous sequence.

Among the alternative approaches, sequences adjacent to the partial sequence can be found by amplification with a primer of the binding sequence and a primer specific to a known region. The amplified sequences are then subjected to a second amplification cycle.

Additional techniques include the capture PCR (Lagerstrom et al., *PCR Methods Applic*. (1991), 1, 111–19) and progressive PCR (Parker et al., *Nucl. Acids. Res*. (1991), 19, 3055–60). Other methods using amplification can also be used to obtain a complete cDNA sequence.

It is possible to obtain a complete cDNA sequence by analyzing the sequences deposited in the public databases "Expressed Sequence Tags" (ESTs) available from GenBank. Research covering the ESTs can be carried out using computer programs which are well known to a person skilled in the art (for example NCBI BLAST) and such ESTs can be used to generate a continuous complete sequence.

Variants of the polynucleotide sequences described above (in particular the sequences SEQ.ID.NO. 4, SEQ.ID.NO. 5 and SEQ.ID.NO. 9) are also included in the field of the present invention. The polynucleotide variants can contain one or more substitutions, deletions or insertions (cf. also above in the part entitled "Polynucleotides, polypeptides and proteins according to the invention").

A portion of the complementary sequence of the coding sequence (i.e. an anti-sense polynucleotide) can also be used as a probe or as a modulator of gene expression. The cDNA constructs capable of being transcribed to anti-sense RNA can be introduced into cells or tissues to facilitate the production of anti-sense RNA. An anti-sense polynucleotide can be used, as described here, to inhibit the expression of a gene associated with the modulation of cell proliferation. Anti-sense technology can be used to control gene expression by forming a triple-helix, which compromises the ability of the double helix to open sufficiently for binding the polymerases, transcription factors or regulation molecules (cf. Gee et al. in Huber and Carr, *Molecular and Immunologic Approaches* (1994), Futura Publishing Co., Mt. Kisco, N.Y.). Alternatively, an anti-sense molecule can be used for hybridizing with a control region of the gene (for example a promoter or a transcription initiation site) and blocking the transcription of the gene, or blocking translation by inhibiting the binding of the ribosomes with the transcript.

The polynucleotides can then be modified by increasing their stability in vivo. Possible modifications include (but are not limited to): the addition of sequences to the 5' and/or 3' ends; the use of phosphorothioate or 2' O-methyl rather than phosphodiesterase bonds in the skeleton; and/or the introduction of bases such as inosine, queosine and wybutosine, similarly acetyladenine, methylthioadenine and other modified forms of adenine, cytidine, guanine, thymine and uridine.

Other variations of the polynucleotides of the present invention have moreover already been described previously in the part entitled "Polynucleotides, polypeptides and proteins according to the invention".

The sequences of nucleotides as described in the present invention can be joined to other nucleotide sequences by using established recombinant DNA techniques. For example, a polynucleotide can be cloned in a large panel of expression vectors, including plasmids, phagemids, derivatives of the lambda phage and cosmids. The vectors of particular interest include expression vectors, replication vectors and sequencing vectors. In general, a vector contains a functional replication origin in at least one organism, suitable endonuclease restriction sites and one or more selection markers. The presence of other elements will depend on the specific use required by a person skilled in the art who will select the characteristic of the expression vector depending on their requirements and the available techniques.

The polynucleotides can be formulated for entering into the cell and expressing the corresponding polypeptide. Such formulations are particularly useful in therapeutics as described hereafter.

Persons skilled in the art will appreciate that several means exist for expressing a polynucleotide in a target cell, and that any suitable techniques can be used. For example, a polynucleotide can be incorporated in a viral vector such as an adenovirus or a retrovirus (but also in others). Techniques for incorporating DNA in such vectors are well known to a person skilled in the art. A retroviral vector can transfer or incorporate a gene for a selection marker and/or a target entity as a gene coding for the ligand of a specific receptor of a target cell, in order to render the vector target-specific.

Other formulations for the polynucleotides include the colloidal dispersion systems such as macromolecular complexes, nano-capsules, microspheres, beads, and systems based on the use of lipids including oil/water emulsions, micelles, mixed micelles and liposomes. The preferred colloidal system used to deliver the product in vitro and in vivo is the liposome (i.e. an artificial membrane vesicle).

Polypeptide Associated with the Modulation of Cell Proliferation

Within the scope of the disclosure, the polypeptides of the present invention include at least one portion of the protein associated with the modulation of cell proliferation or a variant of the latter, said portion being immunologically and/or biologically active. Such polypeptides can be of any length, including the complete protein, an oligopeptide (i.e. consisting of a relatively limited number of amino acids, such as 8–10 residues, joined by peptide bonds) or a peptide of intermediate size. A polypeptide can also include of additional sequences.

A polypeptide is immunologically active, in the context of the present invention, if it is recognized by a surface receptor of the B and/or T cells. The immunological activity can be tested by using standard techniques such as those summarized by Paul, *Fundamental Immunology*, 3$^{rd}$ ed., 243–247 (Raven Press, 1993). Such techniques include the screening of the polypeptides derived from the native polypeptide to determine its ability to react with an antigen-specific antiserum and/or T cell lines or clones being able to be prepared according to standard methods. An immunologically active portion of the protein associated with the modulation of cell proliferation reacts with such antiserums and/or T cells and is not significantly weaker than the reactivity of the complete polypeptide (e.g. in an ELISA test and/or in a T cell reactivity test). Such screenings can generally be carried out using methods well known to a person skilled in the art such as those described in Harlow and Lane, *Antibodies: A Laboratory Manual*, Cold Spring Harbor Laboratory, 1988.

Epitopes of B and T cells can also be predicted by using computer techniques.

Alternatively, the immunogenic portions can be identified by using computer analysis such as the program Tsites® (cf. Rothbard and Taylor, *EMBO J*. (1988), 7, 93–100; Deavin et al., *Mol. Immunol*. (1996), 33, 145–155), which research peptide units having the potential to elicit a response. The peptide units which are suitable for binding to murine or human major histo-compatibility complexes of class I or II (MHC) can be identified according to the BIMAS method (Parker et al., *J. Immunol*. (1994), 152:163, 1994). To confirm the immunogenicity, a peptide can be tested by using a HLA A2 transgenic mouse and/or an in vitro stimulation test using dendritic cells, fibroblasts or peripheral blood cells.

Similarly, a polypeptide is "biologically active" if it has one or more structural, regulatory and/or biochemical functions from the native protein associated with the modulation of cell proliferation. The presence of a biological activity can be determined according to methods well known to a person skilled in the art.

For example, comparison studies of sequences can indicate a particular biological activity of the protein. The tests leading to the evaluation of said activity can then be used on the test base already known in the art. Certain portions and other variants of such proteins would also show this property according to an in vitro or in vivo test.

As has already been mentioned, the polypeptides according to the present invention can include one or more portions of a variant of the endogenous protein where the portion is immunologically and/or biologically active (i.e. the portion has one or more antigenic, immunogenic and/or biological characteristics of the complete protein). Preferably, such a portion is also at least as active as the total protein during testing allowing the detection of such properties. A polypeptide "variant" is a polypeptide which differs from the native protein by substitutions, insertions, deletions and/or modifications in amino acids. Certain variants contain conservative substitutions. A "conservative substitution" is a substitution in which an amino acid is substituted by another amino acid having the same properties, such as those determined by a person skilled in the art who expects no change in the secondary structure, as well as in the hydropathic nature of the polypeptide. The amino acid substitutions can generally be carried out on the basis of similarity of polarity, charge, solubility, hydrophobicity, hydrophilicity, and/or the amphipathic nature of the residues. For example, the negatively-charged amino acids include aspartic acid and glutamic acid; positively-charged amino acids include lysine and arginine; and polar non-charged amino acids having similar hydrophobicity values include leucine, isoleucine and valine; glycine and alanine; asparagine and glutamine; serine, threonine, phenylalanine and tyrosine. Other groups of amino acids which can represent conservative changes are in particular the following: (1) Ala, Pro, Gly, Glu, Asp, Gln, Asn, Ser, Thr; (2) Cys, Ser, Tyr, Thr (3) Val, Ile, Leu, Met, Ala, Phe; (4) Lys, Arg, His; and (5) Phe, Tyr, Trp, His. A variant can also, or alternatively, contain non-conservative changes.

Variants forming part of this invention also include polypeptides in which the primary structure of the native protein is modified by the formation of covalent or non-covalent conjugates with other polypeptides or chemical structures such as lipidic groups or glycosyl, or phosphate acetyl groups.

The present invention also includes polypeptides with or without glycosylation units.

The polypeptides expressed in yeast expression systems or mammalian cells can be, in terms of molecular weight and glycosylation pattern, similar to or slightly different from the native molecule according to the expression system used.

The expression of DNA in bacteria such as *E. Coli* leads to non-glycosylated molecules. The N-glycosylation sites of the eukaryotic proteins are characterized by the triplet of amino acids Asn-A1-Z where A1 is any amino acid except Pro, and Z is a serine or a threonine.

Also included in the present invention are the alleles of the protein associated with the modulation of cell proliferation. The alleles are alternative forms of the native protein resulting from one or more mutations (being able to be suppressed, added or substituted amino acids), leading to an altered RNA. The allelic proteins can differ in the sequence, but the overall structure as well as the function are substantially similar. The protein associated with the modulation of cell proliferation, the variants and the portions of the latter can generally be prepared from nucleic acids coding the desired polypeptide using standard techniques. For preparing the endogenous protein, an isolated cDNA can be used.

Other variations of the polypeptides and proteins of the present invention have moreover already been described previously in the part entitled "Polypeptides and polynucleotides according to the invention".

For preparing a polypeptide variant, standard mutagenesis techniques, such as directed mutagenesis using a directed oligonucleotide, can be used.

In general, any expression vectors known to a person skilled in the art can be used for expressing the recombinant polypeptides of this invention. The expression can be obtained in any appropriate host cell which has been transformed or transfected with an expression vector containing a DNA sequence which codes for the recombinant polypeptide. Suitable host cells include prokaryotic, higher eukaryotic or yeast cells. Preferably, the host cells used are *E. Coli*, yeast cells or mammalian cells such as COS, CHO, MCF7 (human tumor cells isolated from a mammary carcinoma) or DU 145 (human tumor cells isolated from a prostate cancer).

After expression, the supernatant of the host/vector systems which secrete the recombinant protein or polypeptide in the culture medium can in the first instance be concentrated by using standard techniques such as alcoholic precipitation or filtration using commercially-available filters. After the concentration stage, the resulting product can be applied to a suitable purification matrix such as an affinity matrix of or an ion exchange resin. One or more HPLC stages can be used for monitoring the purification of the polypeptide.

Certain portions and other variants can also be generated by synthetic means using techniques which are well known to a person skilled in the art. For example, the portions and other variants having less than 500 amino acids, preferably less than 100 amino acids and more preferentially less than 50 amino acids can be synthesized by chemical route. The polypeptides can be synthesized by using synthesis techniques on solid phase which are commercially available, such as the synthesis method on Merrifield resin where the amino acids are sequentially added to a chain of amino acids during synthesis (cf. Merrifield, *J. Am. Chem. Soc.* (1963), 85, 2149–2146). Numerous other synthesis techniques on solid phase are also available (for example the method of Roberge et al., *Science* (1995), 269, 202–204). Equipment for the automatic synthesis of polypeptides is commercially available from suppliers such as Applied Biosystems, Inc. (Foster City, Calif., USA); the synthesis of the polypeptides can then be carried out by following the manufacturer's recommendations.

Isolated Polynucleotides or Polypeptides

In general, the polypeptides and polynucleotides described in the present invention are isolated. An "isolated" polypeptide or polynucleotide is a polynucleotide or a peptide removed from its original environment. For example, a natural protein is isolated if it is separated from the biological material with which it coexisted in the natural system. A polynucleotide is considered as isolated if, for example, it is cloned in a vector which is not part of the natural environment.

Signal Sequences

The methods for predicting whether a protein has a signal sequence, similarly that for predicting the cleavage point for this sequence, are available. For example, the method of McGeoch (*Virus Res.* (1985), 3, 271–286) uses information on a short N-terminal charged sequence of a non-charged region of the complete protein (not cleaved). The method of Von Heinje (*Nucleic Acid Res.* (1986), 14, 4683–4690) uses information on the residues which surround the cleavage site. The precision of prediction of the cleavage points of the known secreted proteins of mammals for each of these methods is 75–80%. However, the two methods do not always predict the same cleavage sites for a given protein.

In the present case, the deduced amino acids sequence of the secreted polypeptide was analyzed by a computer program called SignalP (Sequence Analysis Software Package from the Genetic Computer Group, University of Wisconsin Biotechnology Center, 1710 University Avenue, Madison, Wis. 53705, USA). This computer program predicts the cellular localization of a protein based on the amino acid sequence.

It is also recognized that, in certain cases, the signal sequence cleavage of a secreted protein is not uniform, thus resulting in the formation of several molecular species. These polypeptides and the polynucleotides coding for these polypeptides are covered by the present invention.

Moreover, the signal sequence identified by the analysis mentioned above cannot predict the natural signal sequence. For example, the natural signal sequence can be upstream or downstream of the predicted sequence. However, it is probable that said signal sequence is capable of directing the secreted protein towards the endoplasmic reticulum. These polypeptides and the polynucleotides coding for these polypeptides are covered by the present invention.

The cleavage sites vary sometimes from one species to another and cannot be predicted with certainty.

The amino acid sequences, starting with methionine, are identified by determined sequences coded by polynucleotides, while other reading frames can be easily translated by using molecular biology techniques which are well known to a person skilled in the art. The polypeptides produced by these alternative open reading frames are also envisaged by this present invention.

Antibodies and Fragments of the Latter

The present invention provides binding agents, such as the antibodies which specifically bind the protein associated with the modulation of cell proliferation. Such an agent is referred to as "specifically binding" to the protein modulating cell proliferation if it reacts at a detectable level (for example by an ELISA test) with a protein associated with the modulation of cell proliferation or a portion or a variant of the latter and does not react in a detectable manner with other proteins. The "binding" refers to a non-covalent association between 2 separate molecules so that a complex is formed. The binding capacity can be evaluated, for example, by determination of the binding constant for the formation of the complex. The binding constant is the value obtained when the value of the concentration of the complex is divided by the product of the values of the concentrations of the components. In general, 2 products are called "bound" when the binding constant reaches 103 l/mol. The binding constant can be determined by using methods well known to a person skilled in the art.

Any agent capable of fulfilling the above criteria can be considered as a binding agent.

In the present invention, a binding agent is preferably an antibody or a fragment of the latter. The antibody can be prepared by any of the techniques available to a person skilled in the art (cf. Harlow and Lane, *Antibodies. A laboratory Manual*, Cold Spring Harbor Laboratory, 1988). In general, the antibodies can be produced by cell culture techniques including the generation of monoclonal antibodies or via transfections of antibody genes into the host cells of bacteria or mammals in order to produce the recombinant antibodies.

Amongst other techniques, it is preferable to use those described hereafter. An immunogen containing the polypeptide is injected into a group of mammals (for example mice, rats, rabbits, sheep or goats). In this stage, the polypeptides of the present invention can serve as immunogens without modification. Alternatively, and particularly for small peptides, a superior immune response can be induced if the polypeptide is joined to a transport protein such as the bovine serum albumin or limpet hemocyanine. The immunogen is injected into the host animal, preferably according to a predetermined schedule, and the animals are bled periodically. Polyclonal antibodies specific to the polypeptide can thus be purified from such antiserums, for example by affinity chromatography using the peptide coupled to a suitable solid support.

Fusion Proteins

Any fusion gene can be produced by a person skilled in the art in order to analyze the subcellular localization of a protein according to the invention, in particular the subcellular localization of the protein of sequence SEQ.ID.NO. 8. Numerous plasmid constructions are commercially available, such as the protein Glutathione S Transferase (GST) or fluorescent proteins such as Green Fluorescent Protein (GFP) or also, and in a non-exhaustive manner, poly-Histidine marking.

Human eukaryotic host cells (for example HEK-293) are sub-cultured for 24 hours before the transfection protocol allowing a normal metabolism of the cells and better transfection efficiency. Increasing concentrations (1, 5 and 10 μg) of vector alone, containing the tag protein (GFP, GST or Tag Histidine) or vector containing the polynucleotide of sequence SEQ.ID.NO. 4, the polynucleotide of sequence SEQ.ID.NO. 5 or the polynucleotide of sequence SEQ.ID.NO. 9, fused with the tag protein have been produced using the reagent Effectene® according to the manufacturer's recommendations (Qiagen).

The cells are then analyzed by confocal microscopy, for example, in order to detect the localization of the protein. If the protein is suspected of being secreted for example, the supernatants are recovered, lyophilized, applied to acrylamide gel and analyzed by the Western blot technique using antibodies directed against the tag protein.

Pharmaceutical Compositions

According to certain aspects of the invention, products such as polypeptides, antibodies and/or nucleic acids can be incorporated in pharmaceutical compositions or vaccines. The pharmaceutical compositions include one or more of these products and one or more pharmaceutically acceptable excipients (transporters). Certain pharmaceutical compositions which can optionally be used as vaccines can comprise one or more polypeptides and an immune response activator, such as an adjuvant or a liposome (in which the product is incorporated). The pharmaceutical compositions and the vaccines can moreover contain an administration system, such as biodegradable microspheres. The pharmaceutical compositions and the vaccines within the scope of the disclosure of the present invention can also contain other products which can be biologically active or inactive.

A pharmaceutical composition or a vaccine can contain DNA coding for one or more polypeptides as described above, such that the polypeptide is generated in situ. As mentioned previously, the DNA can be present in any form of administration known to a person skilled in the art, including nucleic acid, bacterial or viral expression systems. The appropriate nucleic acid expression systems contain the DNA sequences necessary for expression in the patient.

The administration systems based on a bacterium involve the administration of a bacterium (such as Bacillus-Calmette-Guerrin) which expresses an immunogenic portion of the polypeptide at its surface. Preferably, the DNA can be introduced by using a viral expression system (for example a pox virus, a retrovirus or an adenovirus) involving the use of non-pathogenic (defective) agents.

Although any suitable transporter known to a person skilled in the art can be used in pharmaceutical compositions of this invention, the type of transporter will vary according to the administration method chosen. The compositions of the present invention can be formulated for each appropriate administration method, including, for example, the topical, nasal, intravenous, intra-cranial, intra-peritoneal, sub-cutaneous and intramuscular routes.

For parenteral administration, such as a sub-cutaneous injection, the transporter preferably contains water, salt, alcohol, fat, paraffin or a buffer. For oral administration, any transporter mentioned above or a solid transporter, such as mannitol, lactose, starch, magnesium stearate, talc, cellulose, glucose, sucrose and magnesium carbonate can be used. Biodegradable microspheres can also be used as transporters for the pharmaceutical compositions of this invention. For certain topical applications, formulations such as creams or lotions are preferred.

Such compositions can also comprise buffers (for example neutral or phosphate buffered saline solutions), carbohydrates (for example glucose, mannose, sucrose or dextrans), mannitol, proteins, polypeptides or amino acids such as glycine, antioxidants, chelating agents such as EDTA or glutathione, adjuvants (for example aluminium hydroxide) and/or protective agents. Alternatively, the compositions of the present invention can be presented in the form of a lyophilisate. Products can also be encapsulated in liposomes using standard technologies.

According to the invention, each of the varieties of adjuvants can be used in vaccines for inducing the immune response. The majority of the adjuvants contains a substance protecting the antigen from rapid catabolism, such as aluminium hydroxide or mineral oil and an immune-response stimulator such as lipid A, proteins derived from Bordetella Pertussis or *Mycobacterium tuberculosis*. Suitable adjuvants are commercially available such as, for example: Freund's adjuvant and complete adjuvant (Difco Laboratories, Detroit, MIY, USA; Merck Adjuvant 65 (Merck and Company, Inc., Rahway, N.J., USA)), biodegradable microspheres; monophosphoryl lipid A; and cytokines such as GM-CSF or interleukin-2, -7 or -12.

The compositions described above can also be administered in the form of retard formulations (i.e. a formulation such as a capsule or sponge which triggers the slow release of the product after administration). Such formulations can generally be prepared by using technologies well known to a person skilled in the art and administered, for example, by oral, rectal route or by sub-cutaneous implantation or by implantation at the desired target site. The retard formulations can contain a polypeptide, a polynucleotide or an antibody dispersed in a transporter matrix and/or contained in a reservoir protected by a diffusion membrane. The transporters for the use of such formulations are biocompatible and must also be biodegradable; preferably the formulation provides a relatively constant active ingredient release level. The quantity of active product contained in the retard formulation depends on the implantation site.

Anticancer Therapy

According to other aspects of the present invention, the products described can be used in anticancer therapy. In particular, the polynucleotides and polypeptides associated with the modulation of cell proliferation can be used to inhibit growth and induce a modulation of cell proliferation in specific breast or prostate tumors.

Such polypeptides or polynucleotides can also be used for the therapy of numerous carcinomas including melanomas, multiple forms of glioblastomas, carcinomas of the lung as well as colorectal cancers. Agents which activate the expression of such polypeptides or polynucleotides can also be used within the framework of these therapies.

According to these aspects of the invention, the products (which can be polypeptides or nucleic acids) are preferably incorporated in pharmaceutical compositions as described above.

Patients suitable for the therapy are all warm-blooded animals, and preferably humans. A patient eligible for a therapy according to the invention may or may not be diagnosed as having cancer. In other words, the pharmaceutical compositions described above can therefore be used to inhibit the development of a cancer at different stages of the disease (in order to prevent the appearance of a cancer or to treat a patient suffering from a cancer).

The pharmaceutical compositions of the present invention are administered in a manner appropriate to each specific cancer to be treated.

The route, the duration and the frequency of administration will be determined on the basis of the state of the patient, the type and severity of the disease, and the administration method. The, routes and frequencies of administration can vary from one individual to another. In general, the pharmaceutical compositions and the vaccines can be administered by injection (for example by intra-cutaneous, intramuscular, intravenous or sub-cutaneous route), by intra-nasal route (for example by inhalation) or by oral route. Preferably, between 1 and 10 doses can be administered over a period of 52 weeks. Alternative protocols can be appropriate for each patient individually.

In general, an appropriate dosage and a treatment regime contain the active product in a quantity sufficient to provide a therapeutic and/or prophylactic benefit. Such a response can be followed by the establishment of an improved clinical outcome (for example more frequent remissions, survival in the complete, partial or longer absence of the disease) in patients treated, compared with patients not treated or treated with lower doses.

According to other aspects of the present invention, a polypeptide can be administered at doses varying from 100 μg to 5 mg. The molecules of DNA coding for such polypeptides can generally be administered in a quantity sufficient to generate comparable polypeptide levels. Appropriate doses can generally be determined by using experimental models and/or clinical tests. In general, the use of the minimum dose which is sufficient to provide effective therapy is preferred. The patients can generally be monitored with respect to the effectiveness of the therapy using suitable tests for the treatment or prevention conditions which will appear familiar to a person skilled in the art.

Methods of Detection and Monitoring of Cancer

The polypeptides, polynucleotides and antibodies described in the present invention can be used in numerous methods for the detection of cancer in a patient. The presence of polypeptides and/or polynucleotides associated with the modulation of cell proliferation, such as those described in the present invention in host cells is indicative of the differentiation and stopping of cell growth. Thus, the sequences associated with the modulation of cell proliferation can be used as markers of distinction between normal cells and malignant cells (and allow the doctor who interprets the results to diagnose, for example, prostate, breast, lung and colon carcinomas). The sequences associated with the modulation of cell proliferation can also be used as markers for monitoring the treatment.

Methods comprising the use of antibodies can allow the investigator to detect the presence or absence of a polypeptide described in the present invention in any available biological sample. Available biological samples include biopsies of tumorous tissues and of healthy tissues, homogenate or extracts from such tissues obtained from a patient. There are a large number of types of tests known to a person skilled in the art for the use of antibodies for the detection of polypeptide markers in a sample (cf., for example, Harlow and Lane, Antibodies: *A Laboratory Manual*, Cold Spring Harbor Laboratory, 1988).

For example, a test can be carried out according to the Western blot technique, in which a protein preparation is subjected to an electrophoresis gel, transferred onto a suitable membrane and subjected to reaction with an antibody. The presence of an antibody on the membrane can then be detected by using a suitable detection reagent, as described below.

According to other aspects of the invention, tests comprising the use of an antibody immobilized on a solid support bound to the polypeptide can be carried out. The bound polypeptide can be detected using a second antibody or other reagents containing a tag moiety. Alternatively, a competitive test can be used, in which a polypeptide is marked with a tag moiety and allows binding to the antibody immobilized after incubation of the antibody with the sample. The ability of the components of the sample to inhibit the binding of the marked polypeptide to the antibody is indicative of the reactivity of the sample with the immobilized antibody, and thus indicative of the polypeptide concentration in the sample.

The solid support can be any material known to a person skilled in the art onto which the antibody can be attached. For example, the solid support can be a test well in a microtitration plate or a filter made of nitrocellulose or any other suitable membrane. Alternatively, the support can be a bead, glass, plastic material or latex such as polystyrene or polyvinyl chloride. The support can also be a magnetic particle.

The antibody can be immobilized on a solid support using a variety of techniques known to a person skilled in the art and widely described in the scientific literature. Within the context of the present invention, the term "immobilization" refers to both a non-covalent association, such as adsorption, and a covalent bond (which can be a direct bond between the antigen and the functional groups on the support or a bond produced by the use of a binding agent). The immobilization by adsorption to a well of a microtitration plate or a membrane is preferred. In this case, the adsorption can be accomplished by placing the antibody, in a suitable buffer, in the presence of the solid support for a suitable time. The contact time varies according to the temperature, but is typically comprised between 1 hour and 1 day. In general, placing the well of a plastic (polystyrene or polyvinyl chloride, for example) microtitration plate in the presence of a quantity of antibody of 1 pg to 10 ng, and preferably of 100 to 200 ng, is sufficient to immobilize a suitable quantiy of the polypeptide.

A covalent bond of the antibody to a solid support can also be created by reacting the support with a bi-functional reagent which reacts with the support and the fonctional group, such as hydroxyl or an amino group, on the antibody. For example, the antibody can be bound in covalent manner to supports covered with an appropriate polymer by using benzoquinone or by condensation of an aldehyde group on the support with an amine and activated hydrogen on the partner according to standard techniques.

In certain cases, the test for the detection of a polypeptide in a sample is the double antibody "sandwich" test. This test can be carried out by placing the antibody immobilized on a solid support, together with the microtitration plate well, in the presence of the biological sample, such that the polypeptide in the sample can bind the the immobilized antibody. The non-fixed products are eliminated from the polypeptide-antibody complex and a second antibody (containing a tag moiety) capable of binding to different sites of the polypeptide is added. The quantity of secondary antibody which remains bound to the solid support is then determined using an appropriate method specific to the tag moiety.

More specifically, when the antibody is immobilized on the support defined above, the protein-binding sites are typically blocked. Any blocking agent known to a person skilled in the art, such as bovine serum albumin or Tween 20™ (Sigma Chemical Co, St. Louis, Mo., USA) can be used. The immobilized antibody is then incubated with the sample and the polypeptide can bind the antibody. The sample can be diluted in a suitable diluent, such as phosphate buffered saline (PBS) solution before incubation.

In general, the appropriate contact time (i.e. the incubation time) is the period of time sufficient for the detection of the presence of the polypeptide within the sample obtained from an individual. Preferably, the contact time thus defined is sufficient to reach a binding level of at least 95% of that reached with equilibrium between the bound peptide and the non-bound peptide. A person skilled in the art will be aware that the time necessary to reach equilibrium must be determined by measuring the level of binding over a period of time. At ambient temperature, an incubation time of 30 minutes is generally sufficient. The non-bound products can then be removed by washing the solid support with an appropriate buffer such as phosphate buffered saline solution containing 0.1% of Tween 20™. The second antibody, containing a tag moiety, can then be added to the solid support.

The tag moieties preferably include enzymes (such as peroxydase), cofactor substrates, staining inhibitors, luminescent groups, fluorescent groups and biotin. The conjugation of the antibody to the tag moiety can be achieved by using standard methods known to a person skilled in the art.

The second antibody is then incubated with the antibody-polypeptide immobilized complex for a sufficient time allowing detection of the bound polypeptide.

An appropriate time can generally be determined by measuring the level of binding over a period of time. The second non-bound antibody is then removed and the second bound antibody is detected using a tag moiety. The method used for the detection of the tag moiety depends on the nature of the tag moiety. For radioactive groups, scintillation or auto-radiographic counting methods are generally appropriate. Spectroscopic methods can be used to detect staining agents, fluorescent or luminescent groups. Biotin can be detected using avidin, coupled to a tag moiety (together with a radioactive or fluorescent group or an enzyme). The enzymatic tag moieties can generally be detected by the addition of a substrate (generally over a suitable period of time), followed by spectroscopic (or other) analysis of the reaction products.

In order to determine the presence or absence of a cancer, the signal detected by the tag moiety bound to the solid support is generally compared with the signal corresponding to the established value from a non-tumorous tissue. Preferably, the limit value is the average signal obtained when the immobilized antibody is incubated with samples from patients without cancer. In general, a sample generating a signal corresponding to 3 times more or 3 times less than the standard deviation of the predetermined limit value is considered as indicative.

For more details, a person skilled in the art will refer to the following publication: Sackett et al., *Clinical Epidemiology. A basic Science for Clinical Medicine*, p. 106–107 (Little Brown and Co., 1985).

The presence or absence of a cancer in a patient can also be determined by evaluating the levels of mRNA coding for the polypeptide of the present invention in the biological sample (for example a biopsy) relative to a predetermined limit value.

Such an evaluation can be carried out by using a large number of methods known to a person skilled in the art such as, for example, hybridization in situ and amplification by polymerase chain reaction (PCR). The probes and primers used in such methods can generally be generated from the sequences listed in the examples, or from similar sequences identified in other individus. The probes can be used in standard hybridization techniques, and can be marked with a detection agent in order to facilitate the detection of the probe. Such reagents include (but are not limited to): radionucleides, fluorescent stains and enzymes capable of catalyzing the formation of detectable products.

The primers can generally be used in detection methods including polymerase chain reaction (PCR) such as RT-PCR, in which the PCR is used in conjunction with reverse transcription. Typically, the RNA is extracted from a sample tissue and is transcribed in reverse manner for the production of cDNA molecules. The PCR amplification using specific primers generates cDNA molecules associated with the modulation of cell proliferation, which can be separated and visualized using, for example, electrophoresis gel. The amplification is typically carried out on samples obtained from pairs of tumorous and non-tumorous tissues from the same individual, or also from pairs of tumorous and non-tumorous tissues from different individuals. The amplification reaction can be carried out on successive dilutions of cDNA covering 2 orders of magnitude. A modification by a factor of 2 or more of the expression in dilutions of the tumorous sample compared with the same dilutions of the non-tumorous sample is typically considered as indicative.

Certain tests aimed at establishing a diagnosis can moreover be carried out directly on the tumor.

Such a test involves the contact of the tumor cells with an antibody or fragment of the latter which binds a protein associated with the modulation of cell proliferation. The bound antibody or a fragment of the latter can be detected directly or indirectly via a tag moiety. Such antibodies can also be used in histological applications. Alternatively, an anti-sense polynucleotide can be used in such applications.

According to other aspects of the present invention, the progression and/or response to treatment of a cancer can be monitored by carrying out any of the tests described above over a period of time and evaluating the change in response level (i.e. the quantity of polypeptide or mRNA detected). For example, the tests can be carried out monthly over a period of 1 to 2 years. In general, a cancer progresses in patients, in whom the response level diminishes over time. Conversely, a cancer does not progress when the signal detected remains constant or increases over time.

The present invention also provides kits for the use of all the methods of diagnosis described above. Such kits include 2 components (or more) necessary for carrying out such tests. Such components can be the products, the reagents and/or receptacles or equipment. For example, a receptacle inside a kit can contain a monoclonal antibody or a fragment of the latter which specifically binds a polypeptide associated with the modulation of cell proliferation. Such antibodies or fragments can be provided attached to a support material as described above. One or more additional receptacles can contain elements, such as reagents or buffers, to be used in the test. Such kits can also contain a detection reagent (for example an antibody) containing a tag moiety suitable for the direct or indirect detection of the bound antibody.

Methods for the Identification of Binding Modulation Agents

The present invention moreover provides methods for the identification of products which bind and/or which modulate the expression of proteins associated with the modulation of cell proliferation. Such agents can generally be identified when bringing a polypeptide provided in the present invention into contact with a candidate product/agent under conditions and for a time sufficient to allow interaction with the polypeptide and/or its effector (for example its receptor). Each variety of binding test well known to a person skilled in the art can thus be carried out in order to test the capacity of a candidate product to bind with the polypeptide or its effector (for example its receptor).

In other tests, the agents can be screened using cells known as having an increase in the expression of the gene associated with the modulation of cell proliferation. Such cells can be brought into contact with candidate agents and the expression of the gene associated with the modulation of cell proliferation evaluated with respect to the expression observed in the absence of a candidate agent.

Alternatively, candidate products can be screened for their ability to modulate the expression (for example the transcription) of a protein associated with the modulation of cell proliferation. In order to evaluate the effect of a candidate agent on the expression of the protein associated with the modulation of cell proliferation, a promoter or a regulation element of the latter can be bound to a tag gene as described above. Such a construct can be transfected into suitable host cells, which are then brought into contact with the candidate agent.

Said host cells are preferably used for the screening of libraries of small molecules originating from combinatorial chemistry programs. According to this preferred variant, the cells are incubated with the library; the cells are then lysed and the supernatant is analyzed for the activity of the tag gene according to standard protocols.

The products which increase the activity of the tag gene are inducers of the transcription of the gene associated with the modulation of cell proliferation and can thus be used to inhibit the progression of the cancer.

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

EXAMPLES

Example 1

Isolation and Characterization of the cDNA Fragments SEQ.ID.NO. 4 and SEQ.ID.NO. 5

The DNA sequence SEQ.ID.NO. 1, present in the public database containing the ESTs has been adopted (Genbank, access number AA176076), and is reproduced hereafter:

```
  1 ctccatgana tgccactgtt cctgaccagc cgaagtccag gcaggggag gtttccttgt
 61 ccaggaggga gaggacctcc accctctgac ctttcagttt tccatagcag cccagtgtga
121 agctcggcag ngggtgggca gggcatcagg acaagatgaa gatgctggct ctggaatgag
181 gactcccctt ggcataaggg gtagtggctg gcagaggttg cccagctctt ttggaggcca
241 cagggaatag aggtgggtg gtgcttccgt tcctgtgagg cccgccccc tgagccccct
301 ccgtctgctt cttgtttggc agaaatagat gtggggcaca gcctaagaat gatgggaatc
361 tgcccaagct gtgccctctg gggaaatgaa atcttgctcc tcgtgcagct tccccttttc
421 ccttgcgggg tggggctgg gggtgccaag gctccaccct tggaaggggt tgctggggtg
481 ccaagctcca acctttgctc gctggcagaa ggaaggaagc acctcctgta tctttcaggg
541 ncctgaagcc antttgcctc agagaagaga nagtcc
```

From this sequence, a pair of primers 5' Fwd1 and 3' Rev1 of respective sequences SEQ.ID.NO. 2 and SEQ.ID.NO. 3 (reproduced below) was synthesized in order to obtain a probe allowing the cloning of the complete cDNA containing the complete open reading frame coding for the corresponding gene.

The sequences SEQ.ID.NO. 2 and SEQ.ID.NO. 3 are as follows:

```
SEQ. ID.    5'-CTG ACC TTT CAG TTT TCC ATA GC-3'
NO. 2:

SEQ. ID.    5'-ATC TAT TTC TGC CAA ACA AGA A-3'
NO. 3:
```

In an initial phase, a polymerase chain reaction (PCR) is carried out on a series of commercially available cDNA banks by using the primers of sequences SEQ.ID.NO. 2 and SEQ.ID.NO. 3. The reaction conditions include 0.5 µM of Fwd1 (SEQ.ID.NO. 2) and Rev1 (SEQ.ID.NO. 3), 200 µM of deoxynucleotide triphosphates (or dNTPs: dATP, dCTP, dGTP and dTTP), 10 mM Tris-HCl (pH 8.3), 50 mM KCl, 1.5 mM MgCl$_2$ and 0.5 U Taq DNA polymerase in a final volume of 50 µl. The thermal cycle parameters include denaturation at 94° C. for 30 seconds, hybridization of the primers at 60° C. for 1 minute and an extension of polymerization at 72° C. for 30 seconds (with a final extension of 5 minutes).

The products obtained by the PCR are separated on 1% agarose gel and visualized using ethidium bromide staining. The results show a band of 245 base pairs in the cDNA banks from human cerebrum, hypophysis, lung, kidney and intestine (Quantum) and 290 base pairs in a cDNA bank from human breast and prostate. These results are reproduced in FIG. 1.

The products thus obtained by the PCR are purified by electro-elution and are used as a probe for the cloning of the cDNA containing the complete open reading frame using the manufacturer's recommendations for the use of the Clon-Capture cDNA cloning kit (Clontech).

The nucleic acid sequences of the positive clones are determined using an automatic sequencer. These are the sequences SEQ.ID.NO. 4 and SEQ.ID.NO. 5 reproduced hereafter:

```
SEQ. ID. NO. 4:
   1 aggagggtct gaaggtggga gggcagctcc atgagcagcc actgttcctg accagccgaa 61 gtgccaggca gggggaggtt tccatgtcca ggagggagag gacctccacc ctctgacctt 121 tcagttttcc atagcagccc agtgtgaagc tcggcggggg tgggcagggc atcaggacaa 181 gatgaagatg ctggctctgg aatgaggact ccccttgggc taagggtag tggctggcag 241 aggttgccca gctcttttgg aggccacagg aatagaggt gggtggtgc ttccgttcct 301 gtgaggcccg cccccctgag cccctcgtc tgcttcttgt ttggcagaaa tagatgtggg 361 gcacagcccc tagatgatgg gaatctgccc aagctgtgtc ctctggggaa tgaaatcttg 421 ctcctcatgc agcttcccct ttcccttgcg gggtgggggc tggggtgcc aaggctccac 481 ccttggaggg ggttgctggg ggtgccaagg ctccaccctt tgctcgctgg gcagagggaa 541 ggaagcacct ccctgtatgc tctgcagggg ccctgcagg ccactttgcc tcagaggaag 601 gaggagaggt ccctgggaa atgcgcaca cacacacaca cacacacacg cacacacaca 661 cgcacatgca cacacgcacg catgcacaca cacacacata tgtgcagggg tgcagcctaa 721 gtcagtggag ccaggactgg ctgcgcagct gggcctgccc cattcttgga gtccccaggg 781 aatgagcctc aggatccact tcgtcccttg tttctaagcc aggctgcacg gccgttcctg 841 ggtgtgaaag cattctgtcc tgtctccagt cagagggaac cgcccccaaa ctagaaagct 901 aatttccccc gaaggttcat gaagccagag gcatgccctt gggggttggt cgggagaagg 961 gtgagaggca gtgctgtgga aggggcctgg cccctgctgc ctgcgattc SEQ. ID. NO. 5:
   1 aggagggtct gaaggtggga gggcagctcc atgagcagcc actgttcctg accagccgaa 61 gtgccaggca gggggaggtt tccatgtcca ggagggagag gacctccacc ctctgacctt 121 tcagttttcc atagcagccc agtgtgaagc tcggcggggg tgggcagggc atcaggacaa 181 gatgaagatg ctggctctgg aatgaggact ccccttgggc taagggtag tggctggcag 241 aggttgccca gctcttttgg aggccacagg aatagaggt gggtggcaa caggaaatag 301 ggtgtgggct gtagaccata gtgggtgggg tggtgcttcc gttcctgtga ggcccgcccc 361 cctgagcccc ctcgtctgct tcttgtttgg cagaaataga tgtggggcac agcccctaga 421 tgatgggaat ctgcccaagc tgtgtcctct ggggaatgaa atcttgctcc tcatgcagct
```

```
    -continued
481 tcccctttcc cttgcggggt gggggctggg ggtgccaagg ctccaccctt ggaggggggtt 541 gctggggggtg ccaaggctcc acctttgct cgctgggcag agggaaggaa gcacctccct 601 gtatgctctg caggggcccc tgcaggccac tttgcctcag aggaaggagg agaggtcccc 661 tgggaaaatg cgcacacaca cacacacaca cacgcaca cacacgca catgcacaca 721 cgcacgcatg cacacacaca cacatatgtg caggggtgca gcctaagtca gtggagccag 781 gactggctgc gcagctgggc ctgccccatt cttggagtcc ccagggaatg agcctcagga 841 tccacttcgt cccttgtttc taagccaggc tgcacggccg ttcctgggtg tgaaagcatt 901 ctgtcctgtc tccagtcaga gggaaccgcc cccaaactag aaagctaatt tcccccgaag 961 gttcatgaag ccagaggcat gcccttgggg gttggtcggg agaagggtga gaggcagtgc 1021 tgtggaaggg gcctggcccc tgctgcctgc gattc
```

Example 2

Cloning in an Expression Vector of SEQ.ID.NO. 4 and SEQ.ID.NO. 5

The nucleic acid sequences SEQ.ID.NO. 4 and SEQ.ID.NO. 5 give rise to the synthesis of new primers 5' F1 and 3' R1 of respective sequences SEQ.ID.NO. 6 and SEQ.ID.NO. 7 (reproduced hereafter). These sequences respectively contain the HindIII and EcoRI restriction sites.

The sequences SEQ.ID.NO. 6 and SEQ.ID.NO. 7 are as follows:

SEQ. ID. NO. 6: 5'-GCA AGC TTG CGG GGG AGG AGG AGG G-3'

SEQ. ID. NO. 7: 5'-CGG AAT TCC CGG GGG GAA TCG CAG-3'

A PCR reaction is carried out using the same reaction conditions as those described in Example 1 with the primers SEQ.ID.NO. 6 and SEQ.ID.NO. 7. The products obtained by said PCR reaction can be inserted directly into an expression vector of type but in non exclusive manner, pcDNA3.1 (InVitrogen). After the PCR amplification stage, the products are subjected to a HindIII and EcoRI hydrolysis in order to release the ends containing these sequences then purified from the agarosis gel by electroelution.

The sequences SEQ.ID.NO. 4 and SEQ.ID.NO. 5 are then inserted into an expression vector such as for example pcDNA3.1 (InVitrogen). Analysis by digestion by suitable restriction enzymes of different bacterial clones having received said expression vector makes it possible to isolate the bacterial clones containing the new "expression vector/SEQ ID NO 4" or "expression vector/SEQ ID NO 5" construction.

The preparation in large quantities of these plasmid constructions is carried out using a plasmid DNA purification kit (Qiagen).

Properties of the Polynucleotides of Sequences SEQ.ID.NO. 4 and SEQ.ID.NO. 5

Expression of the Polynucleotides of Sequences SEQ.ID.NO. 4 and of SEQ.ID.NO. 5 in Human Tumorous Tissues Preparation of the RNAs From Cell Cultures and Tumorous Tissues The cells in culture or tumorous tissues are kept at −80° C. before the extraction stages of the total RNAs. The extraction of the total RNAs is based on a technique described in the scientific literature (Chomczynski and Sacchi, *Anal. Biochem.* (1987), 162, 156) using the reagent Trizol (Gibco/BRL). The quality of the RNAs thus extracted is analyzed on 1% agarose gel in the presence of ethidium bromide.

Reverse Transcription From the RNAs

The total RNAs are transcribed in reverse manner with Oligo(dT) primers by using the Superscript® reverse transcriptase as suggested in the manufacturer's manual (Gibco/BRL).

Polymerase Chain Reaction (PCR) on Products Obtained From Reverse Transcription

Analysis of the expression of the sequences SEQ.ID.NO. 4 or SEQ.ID.NO. 5 is carrried out by polymerase chain reaction (PCR) on the reverse transcription products by using the primers 5' Fwd1 and 3' Rev1 of respective sequences SEQ.ID.NO. 2 and SEQ.ID.NO. 3. The reaction conditions include 0.5 µM of Fwd1 and of Rev1, 200 µM dNTPs, 10 mM Tris-HCl (pH 8.3), 50 mM KCl, 1.5 mM $MgCl_2$ and 0.5 U Taq DNA polymerase in a final volume of 50 µl. The thermal cycle parameters include denaturation at 94° C. for 30 seconds, hybridization of the primers at 60° C. for 1 minute and an extension of polymerization at 72° C. for 30 seconds (with a final extension of 5 minutes).

The products obtained by the PCR are separated on 1% agarose gel and visualized using ethidium bromide staining.

In certain cases, a hybridization analysis on a nylon membrane was carried out using as a probe the sequence SEQ.ID.NO. 4 marked with alphaP32-dCTP, using a random labelling kit (Pharmacia). The membrane is then washed under conditions of low stringency (2×SSC, 0.1% SDS at 60° C.) then under conditions of high stringency (0.1×SSC, 0.1% SDS at 65° C.). The membrane is then exposed to a Kodak XAR film.

Analysis of the Expression of the Polynucleotides of Sequences seq. Id. No.4 and SEQ.ID.NO. 5 in Breast Tumor Samples Analysis of the expression of the polynucleotides of sequences SEQ.ID.NO. 4 and SEQ.ID.NO. 5 was carried out on 15 tumorous samples surgically removed from patients with breast tumors.

The cDNAs obtained according to the protocol described above were standardized using a G3PDH (Glyceraldehyde 3-phosphate dehydrogenase) marker expressed in a stable manner in order to control variations in the quantity of RNAs or of cDNA between the samples. The PCR reaction products were then hybridized on a nylon membrane according to the protocol described above.

Figure 2:
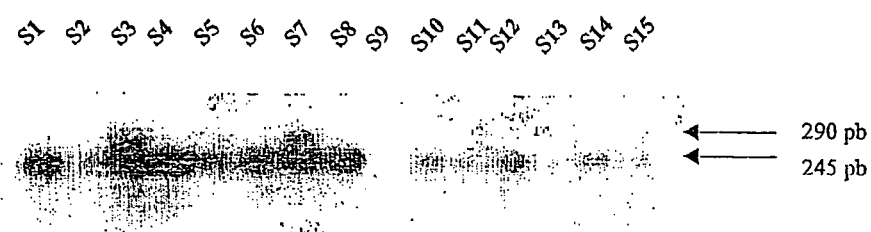
FIG. 2 represents the results obtained by Southern blot on 15 samples of mammary carcinomas (named S1 to S15).

The results obtained, represented in FIG. 2, show that, by this approach, the presence of the polynucleotides of sequences SEQ.ID.NO. 4 and SEQ.ID.NO. 5 can be visualized in tumorous samples from mammary carcinomas.

Inhibition of Cell proliferation by the Polynucleotides of Sequences SEQ.ID.NO. 4 and of SEQ.ID.NO. 5

DU 145 (Code ATCC) prostate tumor cells are cultured in DMEM medium (Dulbecco's Modified Eagle's Medium) containing 100 U/ml of penicillin and 100 µg/ml of streptomycin sulphate, complemented with 10% fetal calf serum. The cells are subcultured 24 hours before the transfection protocol allowing normal metabolism of the cells and better transfection efficiency. Increasing concentrations (1, 5 and 10 µg) of vector alone (pcDNA3.1) or of vector containing the polynucleotide of sequence SEQ.ID.NO. 4 (1, 5 and 10 µg) or the polynucleotide of sequence SEQ.ID.NO. 5 (1, 5 and 10 µg) were achieved using the reagent Effectene® according to the manufacturer's recommendations (Qiagen).

The cells are recovered 48 hours after the transfection by trypsin treatment then counted. At the same temps, the cells are centrifuged at 5000 rpm then frozen at −80° C. for extraction of ARNs as described above (cf. part entitled "*Preparation of the RNAs from cell cultures and tumorous tissues*").

Figure 3:
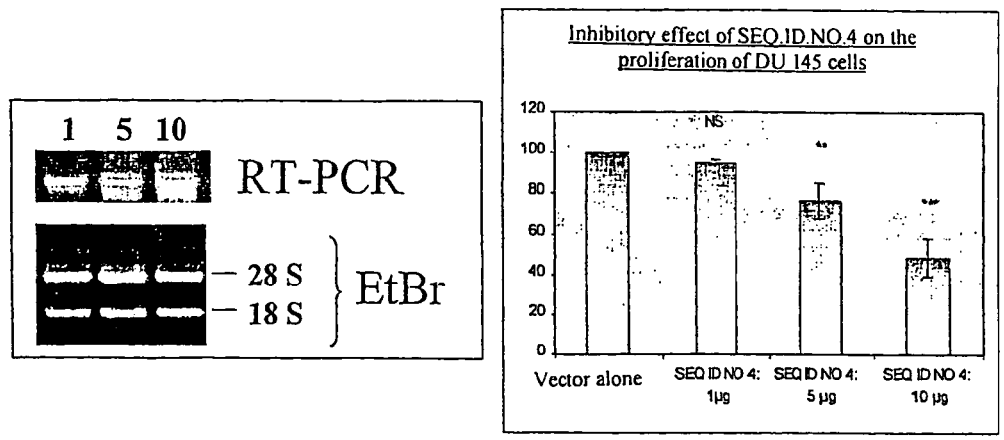
FIG. 3 shows, in its Part A, the expression of the cDNA coding for the polynucleotide of sequence SEQ.ID.NO. 4 in DU 145 (prostate tumor) cells, and in its Part B, the inhibition of the growth of the cells in the presence of increasing concentrations of expression vector containing the polynucleotide of sequence SEQ.ID.NO. 4.
Figure 4:
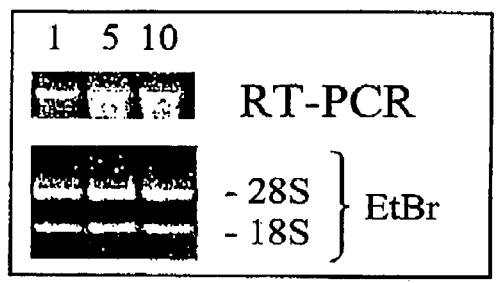
FIG. 4 shows, in its Part A, the expression of the cDNA coding for the polynucleotide of sequence SEQ.ID.NO. 5 in DU 145 (prostate tumor) cells, and in its Part B, the inhibition of the growth of the cells in the presence of increasing concentrations of expression vector containing the polynucleotide of sequence SEQ.ID.NO. 5.
Figure 4:
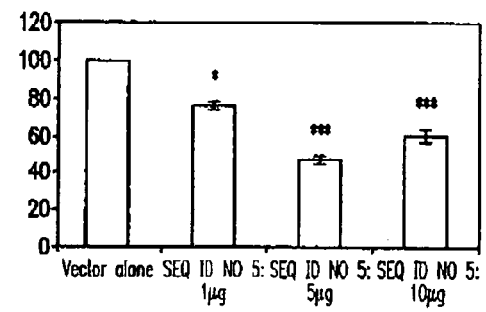

The results are reproduced in FIG. 3 (polynucleotide of sequence SEQ.ID.NO. 4) and FIG. 4 (polynucleotide of sequence SEQ.ID.NO. 5). They indicate that the cDNA coding for the polynucleotide of sequence SEQ.ID.NO. 4 or that coding for the polynucleotide of sequence SEQ.ID.NO. 5 is expressed in proportion to the quantity of expression vector containing the polynucleotide of sequence SEQ.ID.NO. 4 or the polynucleotide of sequence SEQ.ID.NO. 5 (Part A). Moreover, the results indicate that the growth of the cells is significantly inhibited in the presence of increasing concentrations of expression vector containing the polynucleotide of sequence SEQ.ID.NO. 4 or the polynucleotide of sequence SEQ.ID.NO. 5 with respect to the growth of the cells transfected with 10 µg of the vector alone (Part B). The correlation between the inhibition of the growth of the tumorous cells and the quantity of transfected vector containing the polynucleotide of sequence SEQ.ID.NO. 4 or the polynucleotide of sequence SEQ.ID.NO. 5 is equal to 1 or to 0.96 respectively.

Polypeptide Coded From a Fragment of the Sequence SEQ.ID.NO. 5

In the sequence SEQ.ID.NO. 5, an open reading frame is observed with the presence of an initiation codon (ATG) coding for an initiation methionine in position 420 and of a stop codon (UAA) in position 861. A protein of sequence SEQ.ID.NO. 8, made up of 147 amino acids corresponds to the polynucleotide thus translated and is reproduced hereafter:

```
M M G I C P S C V L W G M K S C S S C S F P F P L R G G W    30

G C Q G S T L G G G C W G C Q G S T L C S L G R G K E A P P  60

C M L C R G P C R P L C L R G R R R G P L G K C A H T H T H  90

T H A H T H A H A H T H A C T H T H I C A G V Q P K S V E P  120

G L A Q L G L P H S W S P Q G M S L R I H F V P C F          147
```

The polynucleotide to which the protein of sequence SEQ.ID.NO. 8 corresponds has a nucleotide sequence SEQ.ID.NO. 9 reproduced hereafter:

```
  1 atgatgggaa tctgcccaag ctgtgtcctc tggggaatga aatcttgctc ctcatgcagc 61 ttcccctttc ccttgcgggg tgggggctgg gggtgccaag gctccaccct tggaggggt 121 tgctgggggt gccaaggctc cacccttgc tcgctgggca gagggaagga agcacctccc 181 tgtatgctct gcaggggccc ctgcaggcca ctttgcctca gaggaaggag gagaggtccc 241 ctgggaaaat gcgcacacac acacacacac acacacgcac acacacacgc acatgcacac 301 acgcacgcat gcacacacac acacatatgt gcaggggtgc agcctaagtc agtggagcca 361 ggactggctg cgcagctggg cctgccccat tcttggagtc cccagggaat gagcctcagg 421 atccacttcg tcccttgttt ctaa
```

Legend to the Figures

The invention claimed is:

1. An isolated polynucleotide comprising the polynucleotide sequence of SEQ ID NO: 5.

2. An isolated polynucleotide comprising the full complement of the polynucleotide of claim 1.

3. An isolated polynucleotide comprising the nucleotide sequence of SEQ ID NO: 9.

4. An isolated polynucleotide comprising the full complement of the nucleotide sequence of SEQ ID NO: 9.

5. An isolated polypeptide comprising the amino acid sequence of SEQ ID NO: 8.

6. An expression vector comprising an isolated polynucleotide comprising the nucleotide sequence of SEQ ID NO: 5.

7. A host cell transformed or transfected with an expression vector of claim 6.

8. A composition comprising a polypeptide comprising the amino acid sequence of SEQ ID NO: 8 and a pharmaceutically acceptable excipient.

* * * * *